US007807161B2

(12) United States Patent
Yamamoto et al.

(10) Patent No.: US 7,807,161 B2
(45) Date of Patent: Oct. 5, 2010

(54) HUMANIZED ANTI-HUMAN OSTEOPONTIN ANTIBODY

(75) Inventors: Nobuchika Yamamoto, Chuo-ku (JP); Fumihiko Sakai, Tokyo (JP); Hirofumi Higuchi, Kumamoto (JP); Masaharu Torikai, Kumamoto (JP); Toshihiro Nakashima, Kumamoto (JP)

(73) Assignees: Astellas Pharma Inc., Tokyo (JP); Juridical Foundation The Chemo-Sero-Therapeutic Research Institute, Kumamoto-shi (JP)

( * ) Notice: Subject to any disclaimer, the term of this patent is extended or adjusted under 35 U.S.C. 154(b) by 366 days.

(21) Appl. No.: 11/755,671

(22) Filed: May 30, 2007

(65) Prior Publication Data

US 2009/0053212 A1 Feb. 26, 2009

(30) Foreign Application Priority Data

May 31, 2006 (JP) ............................. 2006-152892

(51) Int. Cl.
*A61K 39/00* (2006.01)
*A61K 39/395* (2006.01)
*C07K 16/46* (2006.01)
*C07K 16/24* (2006.01)

(52) U.S. Cl. .............. 424/133.1; 424/145.1; 530/387.3; 530/388.23

(58) Field of Classification Search ........................ None
See application file for complete search history.

(56) References Cited

U.S. PATENT DOCUMENTS

| 5,854,027 | A | 12/1998 | Steipe et al. | |
|---|---|---|---|---|
| 5,859,205 | A * | 1/1999 | Adair et al. | ............... 530/387.3 |
| 7,241,873 | B2 | 7/2007 | Uede et al. | |
| 7,456,260 | B2 * | 11/2008 | Rybak et al. | ............... 530/387.3 |
| 2004/0234524 | A1 | 11/2004 | Uede et al. | |
| 2008/0138860 | A1 * | 6/2008 | Torikai et al. | ............... 435/69.1 |

FOREIGN PATENT DOCUMENTS

| EP | 0 239 400 | | 9/1987 |
|---|---|---|---|
| EP | 1 637 159 | A1 | 3/2006 |
| WO | WO 90/07861 | | 7/1990 |
| WO | WO 9802462 | A1 * | 1/1998 |
| WO | WO 03/008451 | A2 | 1/2003 |
| WO | WO 03/008451 | A3 | 1/2003 |
| WO | WO 03/027151 | A1 | 4/2003 |
| WO | WO 2006/043954 | | 4/2006 |

OTHER PUBLICATIONS

Nieba et al. Disrupting the hydrophobic patches at the antibody variable/ constant domain interface: improved in vivo folding and physical characterization of an engineered scFv fragment. Protein Engineering vol. 10 No. 4 pp. 435-444, 1997.*

Philip M. Green et al.; "Structural elements of the osteopontin SVVYGLR motif important for the interaction with a4 integrins"; FEBS Letters 503, 2001, pp. 75-79.
Diosdado S. Bautista et al; "Inhibition of Arg-Gly-Asp (RGD)-mediated Cell Adhesion of Osteopontin by a Monoclonal Antibody against Osteopontin"; The Journal of Biological Chemistry, vol. 269, No. 37, Issue of Sep. 16, 1994, pp. 23280-23285.
Simon T. Barry et al.; "Analysis of the a4b1 Integrin-Osteopontin Interation"; Experimental Cell Research 258, 2000, pp. 342-351.
Yasuyuki Yokosaki et al; "The Integrin a9B1 Binds to a Novel Recognition Sequence (svvyglr) in the Thrombin-cleaved Amino-terminal Fragment of Osteopontin" The Jourmal of Biological Chemistry, vol. 274, No. 51 Issue of Dec. 17, 1999, pp. 36328-36334.
U.S. Appl. No. 11/836,078, filed Aug. 8, 2007, Uede, et al.
Stefan Ewert, et al., "Stability improvement of antibodies for extracellular and intracellular applications: CDR grafting to stable frameworks and structure-based framework engineering", Methods: A Companion to Methods in Enzymology, vol. 34, No. 2, XP004526805, Oct. 1, 2004, pp. 184-199.
Arne Wörn, et al., "Stability Engineering of Antibody Single-chain Fv Fragments", Journal of Molecular Biology, vol. 305, No. 5, XP004465987, Feb. 2, 2001, pp. 989-1010.
Yoshiki Saitoh, "Expression of Osteopontin in Human Glioma Its Correlation with the Malignancy"; Laboratory Investigation, vol. 72, No. 1, pp. 55, 1995.
Poul Freese et al.; "Chronic allograft nephropathy-biopsy findings and outcome"; Nephrol Dial Transplant (2001) 16: pp. 2401-2406.
J.R. Waller et al.; "Molecular mechanisms of renal allograft firbosis"; British Journal of Surgery 2001, 88, pp. 1429-1441.
Transplantation, The Official Journal of the Transplantation Society, vol. 72(6), Sep. 27, 2001, pp. 1138-1144.
Anthony O'Regan et al.; "Osteopontin: a key cytokine in cell-mediated and granulomatous inflammation"; Blackwell Scienct Ltd. Int. J. Exp. Path. (2000), 81, pp. 373-390.
Shigeyuki Kon et al.; "Mapping of Functional Epitopes of Osteopontin by Monoclonal Antibodies Raised Against Defined Internal Sequences"; Journal of Cellular Biochemistry, 84: 420-432, 2000.
D. S. Bautista et al; "A Monoclonal Antibody against Osteopontin Inhibits RGD-Mediated Cell Adhesion to Osteopontin"; Annals New York Academy of Sciences, vol. 760, 1995, pp. 309-311.
Nobuchika Yamamoto et al; "Essential role of the cryptic epitope SLAYGLR within osteopontin in a murine model of rheumatoid arthritis"; The Journal of Clinical Investigation, Jul. 2003, vol. 112, No. 2, pp. 181-188.
Georg F. Weber; "The metastasis gene osteopontin: a candidate target for cancer therapy"; Biochimica et Biophysica Acta 1552, (2001), pp. 61-85.
Hema Rangaswami et al; "Osteopontin: role in cell signaling and cancer progression"; Trends in Cell Biology, vol. 16, No. 2, Feb. 2006; pp. 79-87.

(Continued)

*Primary Examiner*—Maher M Haddad
(74) *Attorney, Agent, or Firm*—Oblon, Spivak, McClelland, Maier & Neustadt, L.L.P.

(57) ABSTRACT

The present invention provides a humanized anti-human osteopontin antibody having better activities (antigen binding activity, leukocyte migration inhibitory activity and the like) and/or stability (resistance to heat, low-pH conditions, denaturants and the like) than those of conventional anti-human osteopontin antibodies.

13 Claims, 13 Drawing Sheets

OTHER PUBLICATIONS

Shiva S. Forootan et al; "Prognostic significance of osteopontin expression in human prostate cancer"; Int. J. Cancer: 118, (2006), pp. 2255-2261.

Zhi Hu et al; "Overexpression of Osteopontin is Associated with More Aggressive Phenotypes in Human Non-Small Cell Lung Cancer"; Clin Cancer Res (2005); vol. 11, No. 13, Jul. 1, 2005, pp. 4646-4652.

Sung Sup Park et al.; "Stability of murine, chimeric and humanized antibodies against pre-S2 surface antigen of hepatitis B virus"; Biologicals 31 (2005), pp. 295-302.

Robert F. Kelley et al; "Antigen Binding Thermodynamics and Antiproliferative Effects of Chimeric and Humanized anti-p185HER2 Antibody Fab Fragments"; Biochemistry 1002, 31; pp. 5434-5441, 1992.

William F. Dall'Acqua, et al. "Antibody humanization by framework shuffling" Methods, 36 (2005) pp. 43-60.

ZhuoZhi Wang, et al., "Humanization of a mouse monoclonal antibody neutralizing TNF-α by guided selection", Journal of Immunological Methods, 241 (2000) pp. 171-184.

Manuel Baca, et al, "Antibody Humanization Using Monovalent Phage Display", The Journal of Biological Chemistry, vol. 272, No. 16, Issue of Apr. 18, pp. 10678-10684, 1997.

\* cited by examiner

FIG. 1

```
         10        20        30        40        50        60
CAGCAAGCTTGCCGCCACCATGGAATGGAGCTGGATCTTTCTCTTCCTCCTGTCAGTAAC
    HindIII        M  E  W  S  I  F  L  F  L  L  S  V  T 70        80        90       100       110       120
TGCAGGTGTCCAATCCCAGGTGCAGCTGCAGCAGTCTGGGGCTGAGGTGAAGAAGCCTGG
 A  G  V  Q  S  Q  V  Q  L  Q  Q  S  G  A  E  V  K  K  P  G 130       140       150       160       170       180
GGCCTCCGTGAAGGTCTCCTGCAAGGCTTTGGGGTATACCTTCACTGACTATGAAATGCA
 A  S  V  K  V  S  C  K  A  L  G  Y  T  F  T  D  Y  E  M  H 190       200       210       220       230       240
CTGGGTGAAGCAGACCCCTGTACATGGGCTTGAGTGGATTGGAGCTATTCATCCAGGAAG
 W  V  K  Q  T  P  V  H  G  L  E  W  I  G  A  I  H  P  G  R 250       260       270       280       290       300
AGGTGGTACTGCCTACAATCAGAAGTTCAAGGGCAAGGCCACGCTGACCGCGGACAAATC
 G  G  T  A  Y  N  Q  K  F  K  G  K  A  T  L  T  A  D  K  S 310       320       330       340       350       360
CACTAGTACAGCCTACATGGAGCTGAGCAGCCTGACATCTGAGGACACGGCCGTGTATTA
 T  S  T  A  Y  M  E  L  S  S  L  T  S  E  D  T  A  V  Y  Y 370       380       390       400       410       420
CTGTACAAGAATTACTGGGTACTTCGATGTCTGGGGGCAAGGGACCACGGTCACCGTCTC
 C  T  R  I  T  G  Y  F  D  V  W  G  Q  G  T  T  V  T  V  S 430       440
CTCAGGTGAGTGGATCCGCGA
 S           BamHI
```

FIG. 2

```
           10        20        30        40        50        60
CAGCAAGCTTGCCGCCACCATGGAATGGAGCTGGATCTTTCTCTTCCTCCTGTCAGTAAC
    HindIII         M  E  W  S  I  F  L  F  L  L  S  V  T 70        80        90       100       110       120
TGCAGGTGTCCAATCCCAGGTGCAGCTGGTGCAGTCTGGGGCTGAGCTGGTGAGGCCTGG
 A  G  V  Q  S  Q  V  Q  L  V  Q  S  G  A  E  L  V  R  P  G 130       140       150       160       170       180
GTCCTCCGTGAAGGTCTCCTGCAAGGCTTCTGGGTATACCTTCACTGACTATGAAATGCA
 S  S  V  K  V  S  C  K  A  S  G  Y  T  F  T  D  Y  E  M  H 190       200       210       220       230       240
CTGGGTGAAGCAGACCCCTGTACATGGGCTTGAGTGGATTGGAGCTATTCATCCAGGAAG
 W  V  K  Q  T  P  V  H  G  L  E  W  I  G  A  I  H  P  G  R 250       260       270       280       290       300
AGGTGGTACTGCCTACAATCAGAAGTTCAAGGGCAAGGCCACGCTGACCGCGGACAAATC
 G  G  T  A  Y  N  Q  K  F  K  G  K  A  T  L  T  A  D  K  S 310       320       330       340       350       360
CACTAGTACAGCCTACATGGAGCTGAGCAGCCTGACATCTGAGGACACGGCCGTGTATTA
 T  S  T  A  Y  M  E  L  S  S  L  T  S  E  D  T  A  V  Y  Y 370       380       390       400       410       420
CTGTACAAGAATTACTGGGTACTTCGATGTCTGGGGGCAAGGGACCACGGTCACCGTCTC
 C  T  R  I  T  G  Y  F  D  V  W  G  Q  G  T  T  V  T  V  S 430       440       450
CTCAGGTGAGTGGATCCGCGA
 S           BamHI
```

FIG. 3

```
         10        20        30        40        50        60
CAGCAAGCTTGCCGCCACCATGAAGTTGCCTGTTAGGCTGTTGGTGCTGATGTTCTGGAT
   HindIII          M  K  L  P  V  R  L  L  V  L  M  F  W  I 70        80        90       100       110       120
TCCTGCTTCCAGCAGTGATGTTGTGATGACTCAGTCTCCACTCTCCCTGAGCGTCACCCT
 P  A  S  S  S  D  V  V  M  T  Q  S  P  L  S  L  S  V  T  L 130       140       150       160       170       180
TGGACAGCCGGCCTCCATCTCCTGCAGGAGCTCTCAAAGCATTGTACATAGTAATGGAAA
 G  Q  P  A  S  I  S  C  R  S  S  Q  S  I  V  H  S  N  G  N 190       200       210       220       230       240
CACCTATTTGGAATGGTACCTGCAGAAGCCAGGGCAGTCTCCACAGCTCCTGATCTATAA
 T  Y  L  E  W  Y  L  Q  K  P  G  Q  S  P  Q  L  L  I  Y  K 250       260       270       280       290       300
AGTTTCCAACCGATTTTCTGGGGTCCCAGACAGATTCAGCGGCAGTGGGTCAGGCACTGA
 V  S  N  R  F  S  G  V  P  D  R  F  S  G  S  G  S  G  T  D 310       320       330       340       350       360
TTTCACACTGAAAATCAGCAGGGTTGAAGCTGAAGACGTCGGAGTTTATTACTGCTTTCA
 F  T  L  K  I  S  R  V  E  A  E  D  V  G  V  Y  Y  C  F  Q 370       380       390       400       410       420
AGGTTCACATGTTCCGCTCACGTTTGGCCAGGGGACCAAGCTGGAGATCAAACGTGAGTA
 G  S  H  V  P  L  T  F  G  Q  G  T  K  L  E  I  K  R 430       440       450
GAATTTAAACTTTGCTTCCTCAGTTGGATCCGCGA
                              BamHI
```

FIG. 4

```
            10        20        30        40        50        60
CAGCAAGCTTGCCGCCACCATGAAGTTGCCTGTTAGGCTGTTGGTGCTGATGTTCTGGAT
   HindIII          M  K  L  P  V  R  L  L  V  L  M  F  W  I 70        80        90       100       110       120
TCCTGCTTCCAGCAGTGATGTTGTGATGACTCAGTCTCCACTCTCCCTGCCCGTCACCCT
 P  A  S  S  S  D  V  V  M  T  Q  S  P  L  S  L  P  V  T  L 130       140       150       160       170       180
TGGACAGCCGGCCTCCATCTCCTGCAGGAGCTCTCAAAGCATTGTACATAGTAATGGAAA
 G  Q  P  A  S  I  S  C  R  S  S  Q  S  I  V  H  S  N  G  N 190       200       210       220       230       240
CACCTATTTGGAATGGTACCTGCAGAAGCCAGGGCAGTCTCCACAGCTCCTGATCTATAA
 T  Y  L  E  W  Y  L  Q  K  P  G  Q  S  P  Q  L  L  I  Y  K 250       260       270       280       290       300
AGTTTCCAACCGATTTTCTGGGGTCCCAGACAGATTCAGCGGCAGTGGGTCAGGCACTGA
 V  S  N  R  F  S  G  V  P  D  R  F  S  G  S  G  S  G  T  D 310       320       330       340       350       360
TTTCACACTGAAAATCAGCAGGGTTGAAGCTGAAGACGTCGGAGTTTATTACTGCTTTCA
 F  T  L  K  I  S  R  V  E  A  E  D  V  G  V  Y  Y  C  F  Q 370       380       390       400       410       420
AGGTTCACATGTTCCGCTCACGTTTGGCCAGGGGACCAAGCTGGAGATCAAACGTGAGTA
 G  S  H  V  P  L  T  F  G  Q  G  T  K  L  E  I  K  R 430       440       450
GAATTTAAACTTTGCTTCCTCAGTTGGATCCGCGA
                                BamHI
```

1. Molecular weight marker
2. Complete molecule type R2K1v1.7
3. F(ab')$_2$ of R2K1v1.7
4. F(ab')$_2$-PEG of R2K1v1.7

HUMANIZED ANTI-HUMAN OSTEOPONTIN ANTIBODY

TECHNICAL FIELD OF THE INVENTION

The present invention relates to a humanized anti-human osteopontin antibody having excellent activity and stability, and a therapeutic and diagnostic method for disease using the antibody.

BACKGROUND ART

Osteopontin (hereinafter referred to as "OPN") is an acidic calcium-binding glycoprotein abundantly found in the bone, and in the case of humans, it is known that at least three isoforms can occur due to differences in mRNA splicing: osteopontin-a (hereinafter referred to as "OPN-a"), osteopontin-b (hereinafter referred to as "OPN-b") and osteopontin-c (hereinafter referred to as "OPN-c") (non-patent document 1). In particular, the precursor of OPN-a has the amino acid sequence shown by SEQ ID NO:23 in the sequence listing given below, and is considered to undergo signal peptide cleavage upon secretion to form the mature form OPN-a of I17-N314. The mature form of OPN is cleaved by thrombin in vivo on the C-terminal side of the 168th (in the case of OPN-a) arginine residue, resulting in an N-terminal fragment and a C-terminal fragment.

The above-described OPN is responsible for a wide variety of physiologically and pathologically important functions, and has functions, for example, cell adhesion, cell migration, tumorigenesis, immune responses, inhibition of complement-mediated cytolysis, and the like. These diverse functions are mediated by a wide variety of cell surface receptors. OPN has the RGD sequence therein (for example, for OPN-a, 159th to 161st residues); integrins that recognize this RGD sequence, such as $\alpha V\beta 3$, $\alpha V\beta 1$ and $\alpha V\beta 5$, are major receptors of OPN, of which $\alpha V\beta 3$, $\alpha V\beta 1$ and $\alpha V\beta 5$ integrins mediate cell adhesion in vascular smooth muscle cells; furthermore, $\alpha V\beta 3$ is associated with the migration of macrophages, lymphocytes, endothelial cells, smooth muscle cells and the like.

Furthermore, research that has been conducted to date has also demonstrated that OPN binds to $\alpha 9\beta 1$, $\alpha 4\beta 1$ and $\alpha 9\beta 1$ integrins via the SVVYGLR sequence (SEQ ID NO:10), and a difference in binding mode has been found in that $\alpha 4\beta 1$ binds to both OPN not cleaved by thrombin (non-cleaved type OPN) and an N-terminal fragment cleaved by thrombin (cleaved type OPN), whereas $\alpha 9\beta 1$ binds only to thrombin-cleaved type OPN (non-patent documents 2 to 4). These $\alpha 9$ and $\alpha 4$ and $\beta 1$ and $\beta 7$ integrin subunits are highly similar to each other in terms of amino acid sequence. $\alpha 4\beta 1$ and $\alpha 4\beta 7$ integrins are found mainly in lymphocytes and monocytes but expressed at very low levels in neutrophils. On the other hand, $\alpha 9\beta 1$ is highly expressed selectively in neutrophils, and is responsible for the essential functions for neutrophil migration via VCAM-1, Tenascin-C and the like. $\alpha 9\beta 1$ is widely expressed in myocytes, epithelial cells, hepatocytes and the like. Hence, the cytoplasmic domains of the integrin subunits $\alpha 4$ and $\alpha 9$ are considered to be involved in various inflammatory reactions by cooperatively promoting the migration and aggregation of leukocytes to inflammation sites via respective slightly different intracellular signal transduction pathways to enhance the infiltrating activities thereof.

As described above, because a wide variety of integrins promote the migration of leukocytes and are involved in inflammatory reactions, drugs that inhibit these integrin activities are thought to have the potential for serving as anti-inflammatory agents. For example, integrin $\alpha V\beta 3$ is expressed in osteoclasts, vascular endothelial cells, smooth muscle cells and the like; because inhibiting the binding of $\alpha V\beta 3$ integrin and various binding ligands thereof is expected to have joint destruction suppressive action in, for example, joints, development of anti-$\alpha V\beta 3$ antibody is actually ongoing.

However, because receptors belonging to the integrin family are universally expressed in a broad range of tissues and responsible for the essential functions for the maintenance of biological activities, use of an antibody against integrin in the treatment of rheumatoid arthritis or osteoarthritis can cause similar inhibition in other sites, and the onset of adverse reactions is of concern.

From this viewpoint, attempts have been made to date to clarify the etiology of rheumatoid arthritis, osteoarthritis and the like, and to provide a better therapeutic method.

For example, in WO02/081522 (patent document 1), it was found that in rheumatism patients and osteoarthritis patients, the OPN concentration of articular cavity fluid had high values, and in rheumatism patients, the ratio of thrombin-cleaved type N-terminal fragment to the total OPN increased, and it was confirmed that OPN was profoundly associated with the onset of these diseases. In patent document 1, antibodies that discretely recognize the N-terminal fragment and C-terminal fragment resulting from cleavage of OPN with thrombin, respectively, were generated, and a study using them showed that in rheumatoid arthritis patients, the thrombin-cleaved N-terminal fragment, in particular, exhibited high concentrations in the articular cavity. In this N-terminal fragment, the RGD sequence and the SVVYGLR sequence (SEQ ID NO:10), both recognized by human type integrins, coexist; an antibody that simultaneously blocks these two sequences has been confirmed to be widely inhibit the binding of OPN and integrin, and to be effective in the treatment of rheumatoid arthritis, osteoarthritis and the like.

Specifically, in patent document 1, an antibody that inhibits the binding between the RGD sequence of human OPN and integrin and the binding between the SVVYGLR sequence of human OPN (SEQ ID NO:10) and integrin was generated, and its effect was confirmed by experiments on cell adhesion, cell migration and the like. Furthermore, an antibody against a synthetic peptide corresponding to the internal sequence of mouse OPN was acquired, and its effect as a therapeutic drug was confirmed using a mouse pathologic model of arthritis.

Hence, since mouse OPN has the RGD sequence and the SLAYGLR sequence (SEQ ID NO:12), both recognized by mouse integrin, at positions on amino acid sequence homologous to those of human OPN, the M5 antibody was acquired as an antibody that simultaneously blocks these sequences. It was confirmed that the binding of this M5 antibody to mouse OPN and the thrombin-digested product thereof was inhibited by the GRGDSP peptide, which comprises the RGD sequence, and that this M5 antibody inhibited the migration of TNF-$\alpha$-activated monocytes derived from the mouse spleen. When this M5 antibody was examined using a mouse calvaria organ culture system, bone destruction suppressive action was observed. Furthermore, when the above-described antibody was administered to a mouse model of collagen arthritis, a distinct therapeutic effect was confirmed (patent document 1 and non-patent document 5).

These results strongly suggest that an antibody that simultaneously blocks the binding between the RGD sequence and human type integrin, and between the SVVYGLR sequence (SEQ ID NO:10) and human type integrin inhibits the binding between OPN and integrin and is effective in the treatment of rheumatoid arthritis and the like, and furthermore show that the antibody is expected to be effective not only in the treatment of forms of rheumatism such as juvenile rheumatoid arthritis and chronic rheumatism, but also in the treatment of psoriatic arthritis and psoriasis. Chronic graft rejection after organ transplantation is characterized by obstructive lesions in blood vessels and bronchia; from histological investigations thereof, it is considered that because activation of T cells and macrophages causes production of cytokines and growth factors and vascular endothelial cell disorder, and also because vascular smooth muscle growth causes fibrosis and the like, the condition progresses to vascular obstruction (non-patent documents 6 to 8).

It has been reported that OPN functions as an essential protein in these macrophage activation and vascular smooth muscle fibrosis (non-patent document 9); an OPN inhibitory antibody may suppress the process toward fibrosis by suppressing the migration of monocytes and neutrophils. Therefore, the antibody is expected to suppress chronic graft rejection after organ transplantation to contribute to the take of organs, and to be effective in the treatment of autoimmune diseases such as systemic autoimmune disease, erythematosus, uveitis, Behcet disease, multiple myositis, glomeruloproliferative nephritis, and sarcoidosis. It has also been confirmed that the expression level of OPN increases in various cancers, and that OPN promotes the cancer progression and metastasis (non-patent documents 10 to 12), and that cancer cell growth and metastasis are suppressed by an anti-OPN antibody (patent document 3, non-patent document 13). Therefore, an anti-OPN antibody is also expected to be effective in the treatment of various cancers.

Disclosed in WO03/027151 (patent document 2) are a chimeric anti-human osteopontin antibody having both the variable region of the mouse anti-human osteopontin antibody 2K1 described in patent document 1 and the constant region of a human antibody, and a humanized anti-human osteopontin antibody having both the complementarity determining region of the 2K1 antibody and the framework region and constant region of a human antibody.

Meanwhile, a large number of monoclonal antibodies for treatment are already available in the market, including antibodies for cancer treatment (for example, rituximab, trastuzumab, bevacizumab), antibodies for rheumatism treatment (for example, infliximab, adalimumab), antibodies for treatment for suppressing graft rejection (for example, muromonab, basiliximab) and the like.

Because of their basic features of high specificity and safety, it seems that research and development of monoclonal antibody preparations, particularly targeting a wide variety of diseases for which low-molecular therapeutic drugs are difficult to develop, will be accelerated.

On the other hand, the greatest problem posed in the development of such antibody pharmaceuticals concerns antibody productivity. The clinical doses of monoclonal antibodies that have been launched in the market are generally on the order of several mg/kg, so that considerable production costs are required.

For this reason, to select an antibody that exhibits excellent activity and, out of antibodies showing the same activity, an antibody of high expression levels and high stability for a protein, is a very important requirement for actual application as an antibody pharmaceutical.

Patent document 1: Pamphlet for International Patent Publication No. WO02/081522

Patent document 2: Pamphlet for International Patent Publication No. WO03/027151

Patent document 3: Pamphlet for International Patent Publication No. WO06/043954

Non-patent document 1: Y. Saitoh et al., (1995): Laboratory Investigation, 72, 55-63

Non-patent document 2: Y. Yokosaki et al., (1999): The Journal of Biological Chemistry 274, 36328-36334

Non-patent document 3: P. M. Green et al., (2001): FEBS Letters 503, 75-79

Non-patent document 4: S. T. Barry et al., (2000): Experimental Cell Research 258, 342-351

Non-patent document 5: Yamamoto et al., (2003): The Journal of Clinical Investigation, 112, 181-188

Non-patent document 6: P. Freese et al., (2001): Nephrology, dialysis, transplantation, 16, 2401-2406

Non-patent document 7: J. R. Waller et al., (2001): British Journal of Surgery, 88, 1429-1441

Non-patent document 8: S. R. Lehtonen et al., (2001): Transplantation, 72, 1138-1144

Non-patent document 9: A. O'Regan et al., (2000): International Journal of Experimental Pathology, 81, 373-390

Non-patent document 10: G. F. Weber, (2001): Biochimica et Biophysica Acta, 1552, 61-85

Non-patent document 11: H. Rangaswami et al., (2006): TRENDS in Cell Biology 16, 79-87

Non-patent document 12: S. S. Forootan et al., (2006): Int. J. Cancer: 118, 2255-2261

Non-patent document 13: Z. Hu et al., (2005): Clin. Cancer Res. 11 4646-4652

SUMMARY OF THE INVENTION

The present invention was developed in view of the above-described circumstances, and is intended to provide a humanized anti-human osteopontin antibody having better activities (antigen binding activity, leukocyte migration inhibitory activity and the like) and/or stability (resistance to heat, low-pH conditions, denaturants and the like) than those of conventional anti-human osteopontin antibodies. The present inventors conducted extensive investigations with the aim of accomplishing the object, and succeeded in generating a humanized anti-human osteopontin antibody having such characteristics.

Accordingly, the present invention has the following features:

(1) A humanized anti-human osteopontin antibody comprising a heavy-chain variable region consisting of the amino acid sequence shown by SEQ ID NO:1 and a light-chain variable region consisting of the amino acid sequence shown by SEQ ID NO:3.

(2) The humanized anti-human osteopontin antibody described in (1) above, wherein the heavy-chain constant region of the antibody is human Igγ1.

(3) The humanized anti-human osteopontin antibody described in (1) above, wherein the light-chain constant region of the antibody is human Igκ.

(4) The humanized anti-human osteopontin antibody described in (1) above, wherein the heavy-chain constant region of the antibody is human Igγ1 and the light-chain constant region of the antibody is human Igκ.

(5) A humanized anti-human osteopontin antibody comprising a heavy chain consisting of the amino acid sequence shown by SEQ ID NO:25 and a light chain consisting of the amino acid sequence shown by SEQ ID NO:27.

(6) A polynucleotide comprising a sequence that encodes the heavy-chain variable region of the humanized anti-human osteopontin antibody described in (1) above.

(7) A polynucleotide comprising a sequence that encodes the light-chain variable region of the humanized anti-human osteopontin antibody described in (1) above.

(8) An expression vector comprising the polynucleotide described in (6) and/or (7) above.

(9) A host cell incorporating the expression vector described in (8) above.

(10) A method of producing a humanized anti-human osteopontin antibody, comprising a step for culturing the host cell described in (9) above to allow the cell to express the humanized anti-human osteopontin antibody.

(11) A therapeutic drug for autoimmune disease, rheumatism, rheumatoid arthritis or osteoarthritis, comprising the humanized anti-human osteopontin antibody described in any of (1) to (5) above.

(12) A method for preventing or treating autoimmune disease, rheumatism, rheumatoid arthritis or osteoarthritis, comprising a step for administering a therapeutically effective amount of the humanized anti-human osteopontin antibody described in any of (1) to (5) above.

(13) A use of the humanized anti-human osteopontin antibody described in any of (1) to (5) above, in the manufacture of a pharmaceutical for preventing or treating autoimmune disease, rheumatism, rheumatoid arthritis or osteoarthritis.

Provided by the present invention is a humanized anti-human osteopontin antibody having better activities (antigen binding activity, leukocyte migration inhibitory activity and the like) and/or stability (resistance to heat, low-pH conditions, denaturants and the like) than those of conventional anti-human osteopontin antibodies. Having these features, the antibody of the present invention is useful for the prevention or treatment of various inflammatory diseases, including autoimmune disease, rheumatism, rheumatoid arthritis, and osteoarthritis.

BRIEF DESCRIPTION OF THE DRAWINGS

FIG. 1 shows the base sequence (upper column: SEQ ID NO:15) and amino acid sequence (lower column: SEQ ID NO:16) of a DNA comprising the R2K1-VH1.7 coding region incorporated in a vector (the underlined portion is the leader sequence for secretory expression).

FIG. 2 shows the base sequence (upper column: SEQ ID NO:17) and amino acid sequence (lower column: SEQ ID NO:18) of a DNA comprising the R2K1-VH1.8 coding region incorporated in a vector (the underlined portion is the leader sequence for secretory expression).

FIG. 3 shows the base sequence (upper column: SEQ ID NO:19) and amino acid sequence (lower column: SEQ ID NO:20) of a DNA comprising the R2K1-VL1.7 coding region incorporated in a vector (the underlined portion is the leader sequence for secretory expression).

FIG. 4 shows the base sequence (upper column: SEQ ID NO:21) and amino acid sequence (lower column: SEQ ID NO:22) of a DNA comprising the R2K1-VL1.8 coding region incorporated in a vector (the underlined portion is the leader sequence for secretory expression).

DETAILED DESCRIPTION OF THE INVENTION

Figure 5:
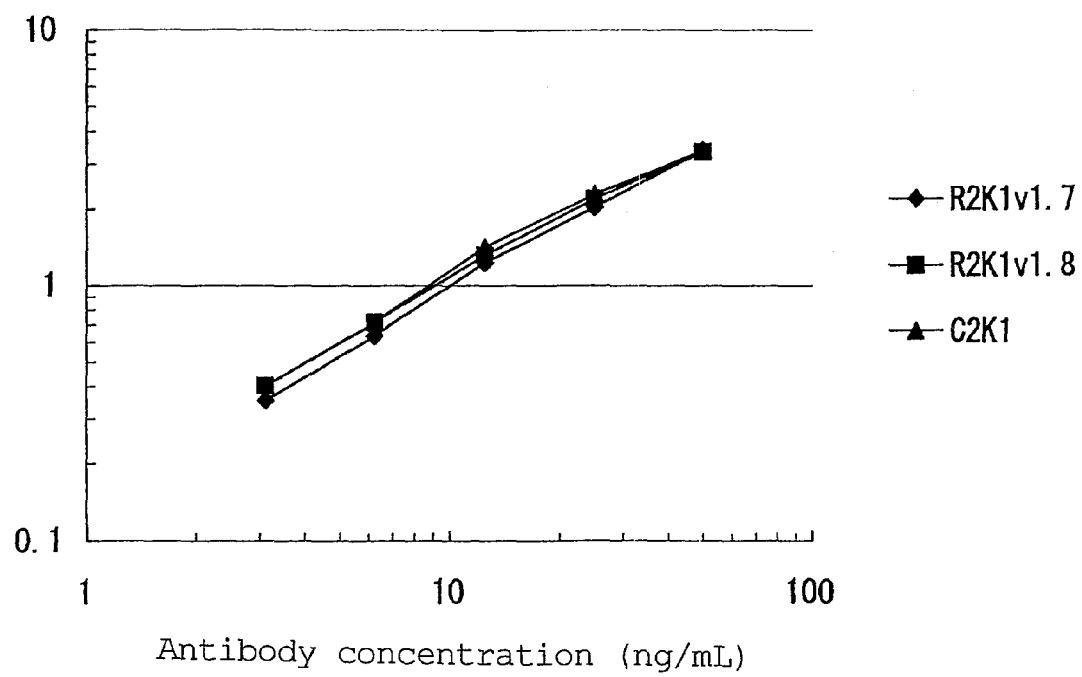
FIG. 5 shows the results of an examination of the bindability of chimeric 2K1 antibody and humanized 2K1 antibody to the hOPN5 peptide by an ELISA method.

The present invention is described in detail below.

The present inventors conducted extensive investigations to solve the above-described problems concerning conventional anti-human osteopontin antibodies, and succeeded in acquiring a humanized anti-human osteopontin antibody having better activities and/or stability than those of the chimeric 2K1 antibody and humanized 2K1 antibody described in WO03/027151 (patent document 2).

The basic structure of an antibody molecule is shared by all classes, and is configured with a heavy chain having a molecular weight of 50000 to 70000 and a light chain having a molecular weight of 20000 to 30000. A heavy chain usually consists of a polypeptide chain comprising about 440 amino acids; heavy chains have structures characteristic of different classes, and are called the γ, μ, α, δ, and ε chains corresponding to IgG, IgM, IgA, IgD, and IgE. Furthermore, IgG occurs as IgG1, IgG2, IgG3, and IgG4, and corresponding chains are called γ1, γ2, γ3, and γ4, respectively. A light chain usually consists of a polypeptide chain comprising about 220 amino acids; two types, type L and type K, are known, and are called the λ and κ chains, respectively. Regarding the peptide configuration of the basic structure of an antibody molecule, two homologous heavy chains and two homologous light chains are bound via disulfide bonds (S—S bonds) and non-covalent bonds, and the molecular weight is 150000 to 190000. The two kinds of light chains are capable of paring with any heavy chain. Each antibody molecule always consists of two identical light chains and two identical heavy chains.

There are four in-the-chain S—S bonds in a heavy chain (five bonds for μ and ε chains) and two in a light chain; one loop is formed per 100 to 110 amino acid residues, and this steric structure is alike among the loops, and is called a structural unit or domain. For both heavy chains and light chains, the amino acid sequence of the domain located at the N terminus thereof is inconstant, even in a reference standard from the same class (subclass) of the same animal species, and this domain is called a variable region (V region, variable region) (the domains are expressed as $V_H$ and $V_L$, respectively). The amino acid sequence on the C-terminal side therefrom is nearly constant in each class or subclass, and is called a constant region (C region, constant region) (the domains are expressed as $C_H1$, $C_H2$, $C_H3$ and $C_L$, respectively).

The antigenic determinant site of an antibody is configured with $V_H$ and $V_L$, and the binding specificity depends on the amino acid sequence of this site. On the other hand, biological activities such as binding to complements or various cells reflect the differences in C region structure among the various classes of Ig. The variability of the variable regions of light chain and heavy chain has been found to be nearly limited to three small hypervariable regions existing in both chains, and these regions are called CDR (complementarity determining region). The remaining portion of the variable region is called a framework region, and is relatively constant. Usually, only 5 to 10 amino acids in the complementarity determining region of each variable region have formed the antigen binding site.

In the present description, an antibody having a variable region derived from a mouse antibody (also referred to as donor heterologous antibody) as the antigen-reactive variable region and a constant region derived from a human antibody as the constant region is referred to as a chimeric antibody; a chimeric antibody that recognizes osteopontin and fragments thereof is referred to as a chimeric anti-osteopontin antibody. A recombinant antibody prepared by replacing all regions, other than the complementarity determining region (antigen binding site), of an antigen specific non-human mammal (for example, mouse) antibody molecule with human antibody amino acids is referred to as a humanized antibody. Included in humanized antibodies are those having an amino acid modification (substitution, insertion, deletion, addition) made to the framework region thereof, like the antibody of the present invention.

It is generally known that in the preparation of a humanized antibody, when the amino acid sequence of the complementarity determining region only is simply grafted to the template human antibody framework, the antigen binding activity decreases compared to that of the original mouse antibody in many cases. The above-described humanized 2K1 antibody was confirmed to have extremely low cell adhesion inhibitory activity on OPN, and hence to be unsuitable for use as an antibody pharmaceutical, though it is bindable to OPN peptides (Example 9 below).

The present inventors conducted extensive investigations to improve the activity reductions in humanized antibodies, and to obtain a humanized antibody having better stability for use as an antibody pharmaceutical, and found that a humanized anti-human osteopontin antibody comprising a heavy-chain variable region consisting of the amino acid sequence shown by SEQ ID NO:1 and a light-chain variable region consisting of the amino acid sequence shown by SEQ ID NO:3 had significantly improved activities and/or better stability in terms of various stability indexes, compared to conventional chimeric and humanized anti-human osteopontin antibodies. As such, the humanized anti-human osteopontin antibody of the present invention has been prepared by making modifications to some amino acids in the framework regions of the heavy chain and light chain of the template human antibody, and has a different sequence of the framework region from that of a conventional humanized anti-human osteopontin antibody prepared by grafting the complementarity determining region only (patent document 2).

The humanized anti-human osteopontin antibody of the present invention can easily be prepared by those skilled in the art on the basis of the sequence information on the heavy-chain variable region and light-chain variable region thereof disclosed herein, using a method commonly known in the art. Specifically, a heavy-chain variable region gene fragment having a base sequence that encodes the heavy-chain variable region amino acid of the antibody of the present invention (SEQ ID NO:1), and a light-chain variable region gene fragment having a base sequence that encodes the light-chain variable region amino acid of the antibody of the present invention (SEQ ID NO:3) are prepared. Then, the variable region genes are joined to a constant region gene in an appropriate class of human antibody to prepare a humanized antibody gene. Next, this humanized antibody gene is joined to an appropriate expression vector, and introduced to a cultured cell. Finally, this cultured cell is cultured, whereby a humanized antibody can be obtained from the culture supernatant.

Each of the above-described variable region gene fragments that encode the heavy-chain and light-chain variable region amino acids of the antibody of the present invention (SEQ ID NO:1 and SEQ ID NO:3) can be prepared by, for example, preparing a gene fragment that encodes the heavy-chain variable region or light-chain variable region, respectively, of the humanized 2K1 antibody, disclosed in WO03/027151, according to the method described in the document, and inducing a mutation to the specified site of the gene fragment that encodes the framework region of the humanized 2K1 antibody. For inducing a mutation at the specified site in the framework region, various methods obvious to those skilled in the art, such as site-directed mutagenesis (Current Protocols in Molecular Biology edit. Ausubel et al. (1987) Publish. John Wiley & Sons Section 8.1-8.5) can be used. Alternatively, gene fragments of the heavy-chain and light-chain variable regions of the antibody of the present invention can also be synthesized on the basis of base sequences designed on the basis of the amino acid sequences of the heavy-chain and light-chain variable regions (SEQ ID NO:1 and SEQ ID NO:3), or on the basis of the base sequences of the heavy-chain and light-chain variable regions of the antibody of the present invention, shown by SEQ ID NO:5 and SEQ ID NO:7, using a method of gene synthesis commonly known in the art. As such a method of gene synthesis, various methods obvious to those skilled in the art, such as the antibody gene synthesis method described in WO90/07861, can be used.

Next, the above-described variable region gene fragments and the constant region gene of the human antibody are joined to prepare a humanized antibody gene. Although any subclass of constant region can be chosen as the constant region of the human antibody used, human Igγ1 as the heavy-chain constant region, and human Igκ as the light-chain constant region, can be preferably used.

Subsequent to the preparation of this humanized antibody gene, introduction of the humanized antibody gene to an expression vector, introduction of the expression vector to cultured cells, cultivation of the cultured cells, purification of the antibody and the like can be performed by using various methods commonly known in the art, or with reference to the methods of preparing a chimeric anti-human osteopontin antibody or a humanized anti-human osteopontin antibody, described in WO02/081522 or WO03/027151. As the expression vector to be joined to the humanized antibody gene thus obtained, the expression vectors described in International Patent Publication Official Gazette WO94/20632, such as AG-γ1 and AG-κ, can be used, but the expression vector is not subject to limitation, as long as it is capable of expressing the humanized antibody gene. It is preferable to utilize an expression vector already having a human Ig constant region gene such as AG-γ1 or AG-κ, because it would become an expression vector having the humanized antibody gene simply when the humanized antibody variable region gene is inserted thereto.

The above-described expression vector is introduced to cultured cells by, for example, the calcium phosphate method and the like.

As examples of the cultured cells to which the expression vector is introduced, cultured cells such as CHO-DG44 cells can be used, and they may be cultured by a conventional method.

After the above-described cultivation, the antibody accumulated in the culture supernatant can be purified by, for example, various chromatographies using a Protein A column.

The antigen activity of the humanized anti-human osteopontin antibody thus obtained can be measured by, for example, an ELISA using an osteopontin peptide and the like as described in an Example below, BIACore (BIAcore Company) and the like. The leukocyte migration inhibitory activity of the humanized anti-human osteopontin antibody can be measured by, for example, culturing human peripheral blood monocytes in the presence of a test antibody and OPN or thrombin-cleaved type OPN as described in an Example below. The humanized anti-human osteopontin antibody of the present invention has a biological activity to inhibit the migration of human peripheral blood monocytes activated by a cytokine (for example, TNF-α) to thrombin-cleaved type OPN.

Next, the humanized anti-human osteopontin antibody thus generated is tested for various stability indexes. The humanized anti-human osteopontin antibody of the present invention exhibits the following stability indexes (A) to D)):

A) Exhibits a heat stability wherein the binding activity to a peptide comprising the SVVYGLR sequence (SEQ ID NO:10) after heat treatment in PBS at 70° C. for 2 hours is not less than 90% of that without the heat treatment.

B) The midpoint transition temperature (Tm) is higher by at least 5° C. than that of a chimeric antibody having a variable region derived from a donor heterologous antibody and a constant region derived from a human antibody.

C) Has a resistance to guanidine hydrochloride at concentrations higher by at least 0.5 M than those for a chimeric antibody having a variable region derived from a donor heterologous antibody and a constant region derived from a human antibody.

D) Has a resistance to pH levels lower by at least 0.3 than those for a chimeric antibody having a variable region derived from a donor heterologous antibody and a constant region derived from a human antibody.

Here, the above-described indexes A) and B) are both indexes of stability to heat; as the antibody has better features in these indexes, it is more advantageous in terms of long-term storage stability and dosage form. That is, an antibody preparation is often problematic with respect to storage stability because it is a protein, so that it is sometimes prepared as a freeze-dried preparation (this is problematic in terms of convenience in medical practice settings because it must be dissolved at the time of use; in particular, a protein preparation often takes more than 30 seconds to dissolve, which in turn often poses a burden in medical practice settings); however, any antibody having a good temperature stability can be stored, even in solution, while securing long-term stability under refrigeration for 2 years or more. In fact, R2K1v1.7, the humanized anti-human osteopontin antibody of the present invention described in an Example below, is secured to be stable for about 1 year even at room temperature (25° C.). If a solution preparation is feasible, it makes it possible to prepare more convenient preparations in the form of pre-filled syringes and the like. An antibody of high temperature stability that satisfies the above-described indexes offers a broader variation of preparation making and makes it possible to make preparations meeting greater medical needs, and to increase choices.

The above-described index C) is an index concerning salt resistance; an antibody having such a salt resistance allows an investigation of a more advantageous formula in making a pharmaceutical preparation. Particularly in pre-filled syringes, this index is useful because high salt concentrations are often used in designing a protein preparation of high concentrations like 100 to 200 μg/mL.

The above-described index D) is an index concerning pH resistance; an antibody having such a pH resistance permits treatment at lower pH levels in the virus inactivation step of the antibody production and purification process, and is hence useful. For this reason, having a pH resistance lower by as small as about 0.3 than ordinary antibodies would be a major advantage.

The test method for index A) is described below. First, a test humanized anti-human osteopontin antibody is diluted in PBS (preferably 50 μg/mL) and heat-treated at 70° C. for 2 hours. Thereafter, the dilution is returned to room temperature, and the binding activity of the antibody to a peptide comprising the SVVYGLR sequence (SEQ ID NO:10) is measured by, for example, the ELISA method of Kon et al. (Journal of Cellular Biology, 88: 420-432 (2002)). The binding activity of this heat-treated antibody is compared with the binding activity of the same antibody but measured without the heat treatment. The humanized anti-human osteopontin antibody of the present invention, when subjected to this heat treatment, exhibits a binding activity not lower than 90% of the binding activity of the same but untreated antibody to peptide comprising the SVVYGLR sequence (SEQ ID NO:10). Preferably, the peptide comprising the SVVYGLR sequence (SEQ ID NO:10), used in this index test, is an osteopontin peptide having the CVDTYDGRGDSV-VYGLRS sequence (SEQ ID NO:13).

The test method for index B) is described below. First, a test humanized anti-human osteopontin antibody and the chimeric 2K1 antibody described in WO03/027151 (C2K1) are adjusted using an appropriate buffer solution (preferably 20 mM citrate buffer+120 mM NaCl (pH 6.0)), and the stability to heating can be evaluated using a differential scanning calorimeter (preferably VP capillary DSC platform of Micro-Cal Company). The midpoint transition temperature (Tm), which shows the degeneration temperature, of the humanized anti-human osteopontin antibody of the present invention is higher by at least 5° C. than that of C2K1.

The test method for index C) is described below. First, a test humanized anti-human osteopontin antibody and the above-described chimeric 2K1 antibody (C2K1) are dissolved in a buffer solution comprising guanidine hydrochloride at various concentrations of 0 to 5 M (preferably 20 mM sodium phosphate+120 mM NaCl solution (pH 7.0)), and the solutions are adjusted to an appropriate concentration (preferably 50 μg/mL). Next, each solution sample is allowed to stand at 10° C. overnight, after which the fluorescent spectrum of each sample is measured. Specifically, the fluorescence emitted by tryptophan under excitation light at 280 nm is scanned over the wavelength range from 320 nm to 370 nm. Peak wavelength shifts due to the loosening of the steric structure of the antibody protein by guanidine hydrochloride. The guanidine hydrochloride concentration for a shift of peak wavelength is measured for each of the test antibody and chimeric antibody. For the humanized anti-human osteopontin antibody of the present invention, the guanidine hydrochloride concentration for a shift of the above-described peak wavelength is higher by at least about 0.5 M than that of C2K1.

The test method for index D) is described below. First, a test humanized anti-human osteopontin antibody and the above-described chimeric 2K1 antibody (C2K1) are adjusted using an appropriate buffer solution (preferably 20 mM citrate buffer+120 mM NaCl (pH 6.0)) (preferably 2 mg/mL), and while an acidic solution (preferably 0.1 N HCl) and water are added thereto, a sample of each low pH level at the specified concentration (1 mg/mL) is prepared. After this sample is treated at room temperature for 1 hour, circular dichroism (CD) spectrum is measured. The CD spectrum is measured over the wavelength range from 205 nm to 260 nm, and the content ratio of random structure is measured for each pH-treated sample of each antibody, on the basis of the CD spectral analytical method of Yang et al. (Methods in Enzymology, 130, 208-269 (1986)). The pH at which the content ratio of random structure in the humanized anti-human osteopontin antibody of the present invention begins to increase is lower by at least about 0.3 than that of C2K1.

The present inventors conducted extensive investigations using in combination modifications of the framework region gene by site-directed mutagenesis and the like, and stability studies using the above-described A) to D) stability indexes, on the basis of the humanized antibody described in WO03/027151, and for the first time succeeded in obtaining a humanized anti-human osteopontin antibody having better activities (antigen binding activity, leukocyte migration inhibitory activity and the like) and/or stability (resistance to heat, low-pH conditions, denaturants and the like) than those of conventional anti-human osteopontin antibodies, by rendering the human antibody framework portions (FR1 to 4) to be the amino acid sequence shown by SEQ ID NO:1 (amino acid numbers 1 to 30, 36 to 49, 67 to 98 and 106 to 116, respectively) and the amino acid sequence shown by SEQ ID NO:3 (amino acid numbers 1 to 23, 40 to 54, 62 to 93 and 103 to 113, respectively). The humanized anti-human osteopontin antibody of the present invention was tested for the above-described antigen binding activity, leukocyte migration inhibitory activity and various stability indexes, and was found to have the activities, and to exhibit all of the indexes A) to D) as characteristics thereof.

The humanized anti-human osteopontin antibody of the present invention, comprising a heavy-chain variable region consisting of the amino acid sequence shown by SEQ ID NO:1 and a light-chain variable region consisting of the amino acid sequence shown by SEQ ID NO:3, can easily be acquired by synthesizing a DNA that encodes the amino acid sequence shown by SEQ ID NO:1 and a DNA that encodes the amino acid sequence shown by SEQ ID NO:3 using a method commonly known in the art, joining them to an appropriate class of human antibody constant region gene, preferably the human Igγ1 constant region gene for the heavy chain and the human Igκ constant region gene for the light chain, to construct a humanized antibody gene, introducing the humanized antibody gene to an expression vector using various methods commonly known in the art or the method described in WO02/081522 or WO03/027151 and the like, introducing the expression vector to cultured cells, culturing the cultured cells, and purifying the antibody from the culture obtained. As the preferable humanized antibody heavy-chain gene of the present invention, obtained by joining the heavy-chain variable region gene shown by SEQ ID NO:1 and the human Igγ1 heavy-chain constant region gene, a gene comprising a base sequence that encodes the amino acid sequence shown by SEQ ID NO:25, more preferably a gene comprising the base sequence shown by SEQ ID NO:24, can be mentioned. As the preferable humanized antibody light-chain gene of the present invention, obtained by joining the light-chain variable region gene shown by SEQ ID NO:3 and the human Igκ light-chain constant: region gene, a gene comprising a base sequence that encodes the amino acid sequence shown by SEQ ID NO:27, more preferably a gene comprising the base sequence shown by SEQ ID NO:26, can be mentioned. As the humanized anti-osteopontin antibody of the present invention, encoded by a heavy-chain gene comprising the base sequence shown by SEQ ID NO:24 and a light-chain gene comprising the base sequence shown by SEQ ID NO:26, R2K1v1.7, described in an Example below, can be mentioned.

Alternatively, the humanized anti-osteopontin antibody of the present invention, comprising a heavy-chain variable region consisting of the amino acid sequence shown by SEQ ID NO:1 and a light-chain variable region consisting of the amino acid sequence shown by SEQ ID NO:3, can also be synthesized with a DNA that encodes the above-described amino acid sequence shown by SEQ ID NO:1 and a human antibody heavy-chain constant region gene, and a DNA that encodes the amino acid sequence shown by SEQ ID NO:3 and a human antibody light-chain constant region gene, as the templates, using a cell-free transcription/translation system. The cell-free transcription/translation system used may be a commercially available one, and may be prepared in accordance with a method known per se, specifically the method described in Pratt J. M. et al., "Transcription and Translation", Hames B. D. and Higgins S. J. edt., IRL Press, Oxford 179-209 (1984) and the like for *Escherichia coli* extract. As the commercially available cell lysate, the *E. coli* S30 extract system (manufactured by Promega Company), the RTS 500 Rapid Translation System (manufactured by Roche Company) and the like derived from *Escherichia coli* can be mentioned, Rabbit Reticulocyte Lysate System (manufactured by Promega Company) and the like derived from rabbit reticulocytes can be mentioned, and PROTEIOS™ (manufactured by TOYOBO Company) and the like derived from wheat germ can be mentioned. Among them, those using a wheat germ lysate is suitable. As a method of preparing a wheat germ lysate, for example, the method described in Johnston F. B. et al., Nature, 179, 160-161 (1957) or Erickson A. H. et al., Meth. Enzymol., 96, 38-50 (1996) and the like can be used.

The present invention also encompasses humanized anti-human osteopontin antibody fragments (antibody fragments) such as single-stranded variable region fragments (scFv), Fab, Fab', and F (ab')$_2$, comprising a heavy-chain variable region consisting of the amino acid sequence shown by SEQ ID NO:1 and a light-chain variable region consisting of the amino acid sequence shown by SEQ ID NO:3, and retaining the activities.

The linker for joining a heavy-chain variable region (VH) and a light-chain variable region (VL), that can be used to prepare scFv, is not subject to limitation, as long as the antibody fragment of the present invention can have the above-descried characteristics; for example, a peptide consisting of the amino acid sequence shown by GGGGSGGGGSGGGGS (SEQ ID NO:14) can be mentioned. Those skilled in the art are able to prepare a fused antibody of the humanized anti-human osteopontin antibody or antibody fragment and another peptide or protein, and to prepare a modified antibody with a modifying agent bound thereto, on the basis of the present invention. The other peptide or protein used for the fusion is not subject to limitation, as long as it does not reduce the binding activity of the antibody; for example, human serum albumin, various tag peptides, artificial helix motif peptide, maltose-binding proteins, glutathione S transferase, various toxins, other peptides or proteins capable of promoting multimerization and the like can be mentioned. The modifying agent used for the modification is not subject to limitation, as long as it does not reduce the binding activity of the antibody; for example, polyethylene glycol, sugar chains, phospholipids, liposomes, low-molecular compounds and the like can be mentioned.

The humanized anti-human osteopontin antibody of the present invention thus obtained or an antibody fragment retaining an activity due to the antibody, a fused antibody resulting from fusion of the antibody or antibody fragment with a peptide or another protein, or a modified antibody consisting of the antibody or antibody fragment and a modifying agent bound thereto, after being further purified as required, can be prepared as a pharmaceutical preparation according to a conventional method, and can be used to treat rheumatoid arthritis, rheumatism such as juvenile rheumatoid arthritis and chronic rheumatism, psoriatic arthritis, psoriasis and the like, to suppress cancer and chronic graft rejection after organ transplantation, and to treat autoimmune diseases such as osteoarthritis, systemic autoimmune disease, erythematosus, uveitis, Behcet disease, multiple myositis, glomeruloproliferative nephritis, and sarcoidosis.

The humanized anti-human osteopontin antibody of the present invention can be used preferably as a rheumatism therapeutic agent, autoimmune disease therapeutic agent, osteoarthritis therapeutic agent or rheumatoid arthritis therapeutic agent, more preferably as a rheumatoid arthritis therapeutic agent. As examples of dosage forms for the rheumatism therapeutic agent and the like, a parenteral preparation such as an injection or drip infusion can be prepared, and is preferably administered by intravenous administration, subcutaneous administration and the like (the same applies in the case of an autoimmune disease therapeutic agent). In preparing a pharmaceutical preparation, carriers and additives that match these dosage forms can be used within a pharmaceutically acceptable range.

The amount of humanized anti-human osteopontin antibody added in the above-described preparation making varies depending on the patient symptom severity and age, the dosage form of the preparation used or the binding titer of the recombinant OPN inhibitory antibody and the like; for example, about 0.1 mg/kg to 100 mg/kg may be used.

Regarding the therapeutic agent of the present invention thus obtained, the active ingredient humanized anti-human osteopontin antibody strongly binds to the RGD sequence and SVVYGLR sequence of OPN (SEQ ID NO:10) to inhibit the binding between this portion of OPN and integrin, resulting in the suppression of the exacerbation of symptoms of rheumatism and rheumatoid arthritis and other autoimmune diseases.

Because the humanized anti-human osteopontin antibody of the present invention binds specifically to the OPN side, rather than to the integrin side, it is unlikely to inhibit any other important function of integrin, and the issue of adverse reactions is expected to be avoided.

Furthermore, the humanized anti-human osteopontin antibody of the present invention can also be used as a diagnostic reagent for rheumatoid arthritis. As stated above, it has been proven that in the joints of a rheumatoid arthritis patient, an N-terminal fragment of thrombin-cleaved OPN are found at high concentrations. Hence, measuring the amount of OPN or N-terminal fragment thereof in a sample using this humanized anti-human osteopontin antibody would be helpful in diagnosing rheumatoid arthritis. As the technique, various methods in use for ordinary immunochemical assays, such as radioisotope immunoassay method (RIA method), ELISA method (E. Engvall et al., (1980): Methods in Enzymol., 70, 419-439), fluorescent antibody method, plaque method, spot method, agglutination method, and Ouchterlony method ("Hybridoma Method and Monoclonal Antibodies", published by R&D Planning, pages 30-53, Mar. 5, 1982) can be used.

Although an appropriate one can be selected from among the above-described techniques from various viewpoints, the ELISA method is preferable in terms of sensitivity, convenience and the like. As an example of a more preferable method, for example, the humanized anti-human osteopontin antibody of the present invention is immobilized on a carrier, an antibody that recognizes a portion on OPN other than that recognized by the humanized anti-human osteopontin antibody of the present invention is labeled, whereby OPN or an N-terminal fragment thereof can be detected, and this can be used as a diagnostic reagent for rheumatoid arthritis.

As the labeling substance used to label the above-described antibody, proteins/peptides for forming a fused protein/peptide, such as glutathione S-transferase, enzymes such as horseradish peroxidase (hereinafter referred to as "HRP") and alkaline phosphatase (hereinafter referred to as "AP"), fluorescent substances such as fluorescein isocyanate and rhodamine, radioactive substances such as $^{32}$P and $^{125}$I, and modifying agents such as chemiluminescent substances can be mentioned.

Regarding the method of detecting OPN isoforms, for example, the detection can be performed by using a method commonly known in the art, such as a sandwich method, or more specifically, by using the same method as the detection method described in WO02/081522 (patent document 2) or WO03/027151 (patent document 3).

The present invention also provides a gene that encodes the antibody of the present invention or a fragment thereof, and an expression vector comprising the same. The expression vector of the present invention is not subject to limitation, as long as it is capable of expressing a gene that encodes the antibody of the present invention or a fragment thereof in various host cells of prokaryotic cells and/or eukaryotic cells, and producing these polypeptides. For example, plasmid vectors, viral vectors (for example, adenovirus, retrovirus) and the like can be mentioned.

The expression vector of the present invention can comprise a gene that encodes the antibody of the present invention or a fragment thereof, and a promoter functionally joined to the gene. As the promoter for expressing the polypeptide of the present invention in a bacterium, when the host is a bacterium of the genus *Escherichia*, for example, the Trp promoter, lac promoter, recA promoter, XPL promoter, lpp promoter, tac promoter and the like can be mentioned. As the promoter for expressing the antibody of the present invention or a fragment thereof in yeast, for example, the PH05 promoter, PGK promoter, GAP promoter, and ADH promoter can be mentioned; when the host is a bacterium of the genus *Bacillus*, the SL01 promoter, SP02 promoter, penP promoter and the like can be mentioned. When the host is a eukaryotic cell such as a mammalian cell, the SV40-derived promoter, retrovirus promoter, heat shock promoter and the like can be mentioned.

When a bacterium, particularly *Escherichia coli*, is used as the host cell, the expression vector of the present invention can further comprise an initiation codon, a stop codon, a terminator region and a replicable unit. When a yeast, animal cell or insect cell is used as the host, the expression vector of the present invention can comprise an initiation codon and a stop codon. In this case, an enhancer sequence, noncoding regions on the 5' side and 3' side of a gene that encodes the polypeptide of the present invention, a splicing junction, a polyadenylation site, or a replicable unit and the like may be contained. A selection marker in common use (for example, tetracycline, ampicillin, kanamycin) may be contained according to the intended use.

The present invention also provides a transformant incorporating the gene of the present invention. Such a transformant can be prepared by, for example, transforming a host cell with the expression vector of the present invention. The host cell used to prepare a transformant is not subject to limitation, as long as it matches the aforementioned expression vector, and is transformable; various cells such as natural cells or artificially established lines of cells in common use in the technical field of the present invention (for example, bacteria (bacteria of the genus *Escherichia*, bacteria of the genus *Bacillus*), yeasts (the genus *Saccharomyces*, the genus *Pichia* and the like), animal cells or insect cells (for example, Sf9) and the like) can be mentioned as examples. The transformation can be performed by a method known per se.

The present invention also provides a method of producing the antibody of the present invention or a fragment thereof, comprising allowing a host cell to express the gene of the present invention, i.e., using such a transformant.

In producing the antibody of the present invention or a fragment thereof, the transformant can be cultured in nutrient medium. The nutrient medium preferably contains a carbon source and an inorganic nitrogen source or organic nitrogen source required for the growth of the transformant. As examples of the carbon source, glucose, dextran, soluble starch, sucrose and the like can be mentioned; as examples of the inorganic nitrogen source or organic nitrogen source, ammonium salts, nitrates, amino acids, corn steep liquor, peptone, casein, meat extract, soybean cake, potato extract and the like can be mentioned. If desired, other nutrients (for example, inorganic salts (for example, calcium chloride, sodium dihydrogen phosphate, magnesium chloride), vitamins, antibiotics (for example, tetracycline, neomycin, ampicillin, kanamycin and the like) and the like) may be contained.

Cultivation of the transformant can be performed by a method known per se. Cultivation conditions, for example, temperature, pH of the medium, and cultivation time are selected as appropriate. For example, when the host is an animal cell, an MEM medium containing about 5 to 20% fetal bovine serum (Science, Vol. 122, p. 501, 1952), DMEM medium (Virology, Vol. 8, p. 396, 1959), RPMI1640 medium (J. Am. Med. Assoc., Vol. 199, p. 519, 1967), 199 medium (Proc. Soc. Exp. Biol. Med., Vol. 73, p. 1, 1950) and the like can be used as the medium. The pH of the medium is preferably about 6 to 8, cultivation is normally performed at about 30 to 40° C. for about 15 to 72 hours, and the culture may be aerated or agitated as necessary. When the host is an insect cell, for example, Grace's medium comprising fetal bovine serum (Proc. Natl. Acad. Sci. USA, Vol. 82, p. 8404, 1985) and the like can be mentioned, and the pH thereof is preferably about 5 to 8. Cultivation is normally performed at about 20 to 40° C. for 15 to 100 hours, and the culture may be aerated or agitated as necessary. When the host is a bacterium, an *actinomyces*, yeast, or a filamentous fungus, for example, a liquid medium comprising the above-described nutrient sources is appropriate. A medium having a pH of 5 to 8 is preferable. When the host is *E. coli*, LB medium, M9 medium (Miller et al., Exp. Mol. Genet, Cold Spring Harbor Laboratory, p. 431, 1972) and the like can be mentioned as preferable media. In this case, cultivation can be normally performed at 14 to 43° C. for about 3 to 24 hours, while aerating or agitating the culture as necessary. When the host is a bacterium of the genus *Bacillus*, cultivation can be normally performed at 30 to 40° C. for about 16 to 96 hours, while aerating or agitating the culture as necessary. When the host is yeast, Burkholder's minimal medium (Bostian, Proc. Natl. Acad. Sci. USA, Vol. 77, p. 4505, 1980) can be mentioned as examples of the medium, and the pH is desirably 5 to 8. Cultivation is normally performed at about 20 to 35° C. for about 14 to 144 hours, and the culture may be aerated or agitated as necessary.

The antibody of the present invention or a fragment thereof can be recovered, preferably isolated and purified, from a cultured transformant as described above. As examples of the method of isolation and purification, methods based on differences in solubility, such as salting-out and solvent precipitation; methods based on differences in molecular weight, such as dialysis, ultrafiltration, gel filtration, and sodium dodecyl sulfate-polyacrylamide gel electrophoresis; methods based on differences in electric charge, such as ion exchange chromatography and hydroxyl apatite chromatography; methods based on specific affinity, such as affinity chromatography; methods based on differences in hydrophobicity, such as reverse phase high performance liquid chromatography; methods based on differences in isoelectric point, such as isoelectric focusing; and the like can be mentioned.

The present invention has been generally described above; particular examples to be referred to for facilitating the understanding thereof are given below, which, however, are for illustrative purposes only and never limit the scope of the invention.

EXAMPLES

Examples are given below. The procedures involving the use of a kit and the like were performed as directed in the protocol attached thereto unless otherwise stated.

(1. Preparation of Humanized 2K1 Antibody)

In the present invention, two kinds of humanized anti-human osteopontin antibody prepared by humanizing the 2K1 antibody, which is a mouse-derived anti-human osteopontin antibody described in International Patent Publication Official Gazette WO2003/027151 (hereinafter also referred to as humanized 2K1 antibody or R2K1 antibody) were prepared.

Since each humanized 2K1 antibody was prepared generally in accordance with the method described in the above-described official gazette, an outline is given below.

First, DNAs that encode the heavy-chain variable regions (VHs) of 2 kinds of humanized anti-OPN antibody having the base sequences shown in FIG. 1 and FIG. 2 and DNAs that encode the light-chain variable regions (VLs) of 2 kinds of humanized anti-OPN antibody having the base sequences shown in FIG. 3 and FIG. 4 were prepared by a PCR using a synthetic oligo-DNA. In the description below, to distinguish them, the humanized anti-human OPN antibody VHs shown in FIG. 1 and FIG. 2 are referred to as R2K1-VH1.7 and R2K1-VH1.8, respectively. Likewise, the humanized anti-human OPN antibody VLs shown in FIG. 3 and FIG. 4 are referred to as R2K1-VL1.7 and R2K1-VL1.8, respectively.

Next, each of the above-described DNAs that encode the humanized anti-human OPN antibody VHs was inserted to AG-γ1, which is an expression vector comprising the gene for the human immunoglobulin constant region γ1 chain, using a restriction endonuclease HindIII recognition site and BamHI recognition site, whereby a heavy-chain expression plasmid having R2K1-VH1.7 and a heavy-chain expression plasmid having R2K1-VH1.8 were prepared. Likewise, each of the above-described DNAs that encode the humanized anti-human OPN antibody VLs was inserted to AG-κ, which is an expression vector comprising the gene for the human immunoglobulin constant region κ chain, whereby a light-chain expression plasmid having R2K1-VL1.8 and a light-chain expression plasmid having R2K1-VL1.7 were prepared. These expression plasmids were introduced to and proliferated in *Escherichia coli*, and purified using a commercially available plasmid purification kit (QIAGEN Company).

Finally, various combinations of the above-described purified expression plasmids were transfected to CHO-DG44 cells by the calcium phosphate method, and cells were selected in an MEM medium (Invitrogen Company) comprising Geneticin (Invitrogen Company) and dialyzed FCS (Invitrogen Company), whereby cells expressing two kinds of humanized 2K1 antibody were obtained. That is, the R2K1v1.8 antibody, which is a humanized 2K1 antibody consisting of a heavy chain having R2K1-VH1.8 and a light chain having R2K1-VL1.8, and the R2K1v1.7 antibody, which is a humanized 2K1 antibody consisting of a heavy chain having R2K1-VH1.7 and a light chain having R2K1-VL1.7, were expressed.

Cells producing each R2K1 antibody, obtained by the above-described procedures, were allowed to grow thoroughly in a MEM medium supplemented with 10% dialyzed FCS, sown to a roller bottle (BD Biosciences Company), and cultured under the conditions of 37° C. and a rotation rate of 1 rpm. Several days later, cells were confirmed to adhere to and grow on the vessel wall, the culture broth was discarded, the medium was exchanged with 500 mL of serum-free MEM medium, and the cells were cultured under the conditions described above. About 2 weeks later, when many cells were suspending off from the vessel wall, the cultivation was stopped, and the culture supernatant was filtered through a 0.22 μm filter and recovered to yield a culture supernatant containing each R2K1 antibody.

With these culture supernatants as the starting materials, and using a Protein A column (MILLIPORE Company) and an anion exchange column (Amersham Company), several milligrams of each of two kinds of purified humanized antibody, that is, the R2K1v1.8 antibody and the R2K1v1.7 antibody, were obtained.

In the various experiments described below, the purified antibodies obtained as described above were used. The chimeric 2K1 antibody (hereinafter also referred to as C2K1 antibody) used was obtained by the method described in the aforementioned International Patent Publication Official Gazette WO2003/027151.

(2. Confirmation of Bindability with Human Osteopontin Peptide by ELISA)

The binding activities of each R2K1 antibody and the C2K1 antibody to a human osteopontin peptide (CVD-TYDGRGDSVVYGLRS: SEQ ID NO:13) were compared with reference to the ELISA method of Kon et al. (Journal of Cellular Biology, 88:420-432 (2002)). An outline is given below.

The peptide having the above-described sequence (hereinafter also referred to as the hOPN5 peptide) was reacted with BSA incorporating a maleimide group introduced using Sulfo-EMCS (Dojindo Laboratories) to prepare a hOPN5-BSA conjugate. The hOPN5-BSA conjugate was immobilized at 200 ng/100 μL/well on an ELISA plate (Nunc Company) at 4° C. overnight, and the plate was washed, after which blocking was performed with PBS supplemented with 1% BSA at 4° C. overnight. An antibody sample diluted with PBS supplemented with 1% BSA was added to the plate at 100 μL/well, and they were reacted at 37° C. for 1 hour. Detection was performed using a peroxidase (HRP)-labeled anti-human IgG (H+L) antibody (Wako Pure Chemical Industries, Ltd.). Absorbance at a wavelength of 450 nm was measured using a microplate reader (Molecular Devices Company).

As a result, it was confirmed that the bindabilities of the R2K1v1.7 antibody and the R2K1v1.8 antibody to the hOPN5 peptide were equivalent to that of the C2K1 antibody (FIG. 5).

(3. Inhibitory Activity of the R2K1 Antibody on Human Peripheral Blood Monocyte Migration)

The inhibitory activity of purified antibody on cytokine-activated peripheral blood monocyte migration was examined as described below.

First, heparinized blood drawn from a healthy person was diluted 2 fold with RPMI1640 medium. The diluted blood was overlain on Ficoll-Paque (Pharmacia K.K.), and centrifuged at 400×g and room temperature for 30 minutes. The white layer seen in the interface between the plasma and the Ficoll-Paque was recovered and used as monocytes. The monocytes thus obtained were cultured and activated with human TNF-α (20 ng/mL) overnight, and used in migration experiments.

The migration experiments were performed using a 48-well microchemotaxis chamber (Neuro Probe Inc.). Human OPN was cleaved by a reaction with bovine thrombin (Sigma) at 37° C. for 2 hours. Each of the R2K1 antibody and the C2K1 antibody was added at various concentrations, and the mixture was allowed to stand at 37° C. for 15 minutes, after which it was added to the lower chamber (the final concentration of human OPN was 10 μg/mL). Mounted thereon was a polycarbonate filter (pore size 5 μm), and 50 μL of a cell suspension ($2 \times 10^6$ cells/mL) was added to the upper chamber.

After cultivation at 37° C. in the presence of 5% $CO_2$ for 2 hours, the polycarbonate filter was removed, the cells on the surface of the upper filter were removed, after which the cells were stained with Diff-Quick (Baxter Company). The cell number on the surface of the upper filter was counted under ×40 magnification, and the results were expressed as the mean cell count (cells/mm$^3$)±SEM for 6 wells (Table 1). From these results, both the R2K1v1.7 antibody and the R2K1v1.8 antibody inhibited the migration of TNF-α-activated human peripheral blood monocytes to thrombin-cleaved human osteopontin as with the C2K1 antibody.

TABLE 1

|  | Mean cell count | SEM |
| --- | --- | --- |
| R2K1v1.7 & R2K1v1.8 | | |
| Medium | 701.7 | 24.8 |
| Thr-OPN | 881.7 | 24.0 |
| R2K1v1.7 50 µg/mL | 723.3 | 43.0 |
| R2K1v1.8 50 µg/mL | 688.3 | 16.6 |
| C2K1 | | |
| Medium | 686.7 | 15.9 |
| Thr-OPN | 860.0 | 30.7 |
| C2K1 50 µg/mL | 671.7 | 48.5 |

(4. Evaluation of Heat Stability by ELISA)

Figure 6:
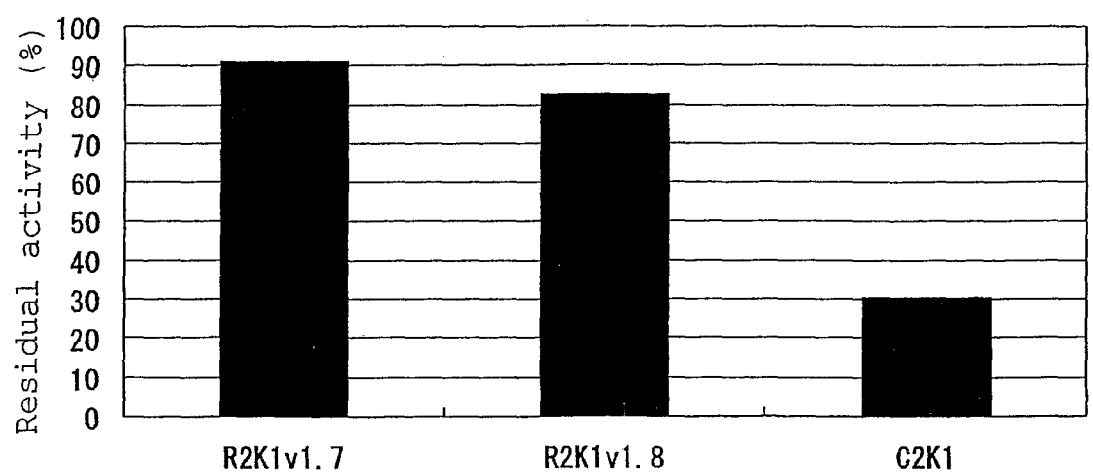
FIG. 6 shows the results of an examination of the bindability of chimeric 2K1 antibody and humanized 2K1 antibody, heat-treated at 70° C., to the hOPN5 peptide by an ELISA method. Ratios to the bindability without the heat treatment as 100% are shown.

Each of the C2K1 antibody and the two kinds of R2K1 antibody was diluted to 50 µg/mL with PBS, and treated in a 70° C. water bath for 2 hours. Thereafter, each dilution was returned to room temperature, and the ratio of the absorbance obtained by the above-described ELISA to the absorbance of an untreated sample was graphed as residual activity. The residual activity was calculated using absorbance values falling in the range from 0.2 to 2.0 with linearity (the same applies below). As a result, it was found that the residual activity after the above-described treatment was higher for the R2K1v1.7 antibody and the R2K1v1.8 antibody than for the C2K1 antibody (FIG. 6). Particularly, the R2K1v1.7 antibody exhibited a residual activity exceeding 90%. This demonstrated that the R2K1v1.7 antibody and the R2K1v1.8 antibody had improved heat stability compared to the C2K1 antibody.

(5. Evaluation of Low-pH Resistance by ELISA)

Figure 7:
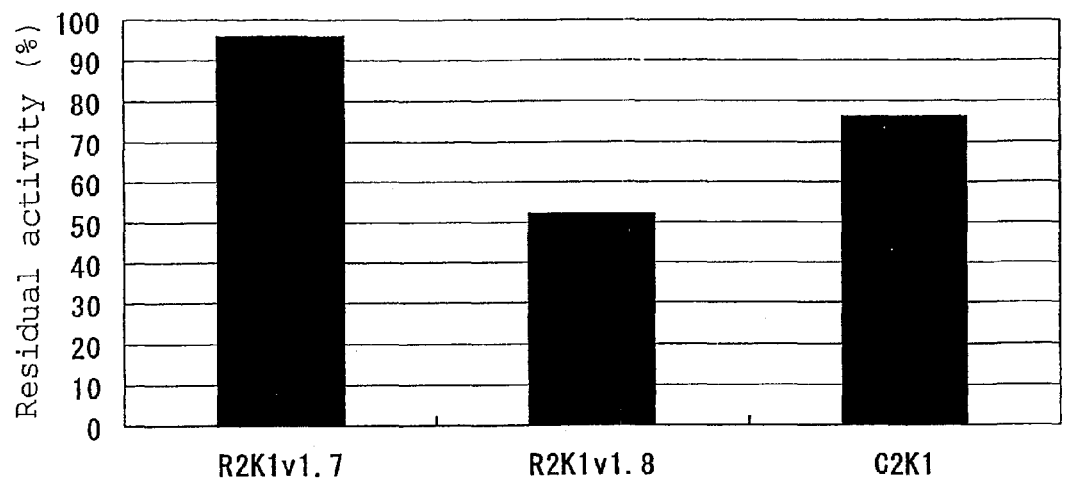
FIG. 7 shows the results of an examination of the bindability of chimeric 2K1 antibody and humanized 2K1 antibody, treated with a buffer at pH 5, to the hOPN5 peptide by an ELISA method. Ratios to the bindability without the pH 5 buffer treatment as 100% are shown.

Each of purified supplies of the C2K1 antibody and the two kinds of R2K1 antibody was diluted with PBS to 50 µg/mL. Each dilution was adjusted to pH 5 with 1 N HCl using a pH meter (HORIBA Company), and treated at 25° C. for 2 hours. Thereafter, the dilution was adjusted to pH 7 with 1 M Tris-HCl (pH 9.5), and the ratio of the absorbance obtained by the above-described ELISA to the absorbance of an untreated sample was graphed as residual activity. As a result, it was found that the residual activity after the above-described treatment was significantly higher for the R2K1v1.7 antibody than for the C2K1 antibody and the R2K1v1.8 antibody (FIG. 7). This demonstrated that the R2K1v1.7 antibody had improved resistance to low pH compared to the R2K1v1.8 antibody and the C2K1 antibody.

(6. Evaluation of Guanidine Hydrochloride Resistance by Fluorescent Spectrometry)

Figure 8:
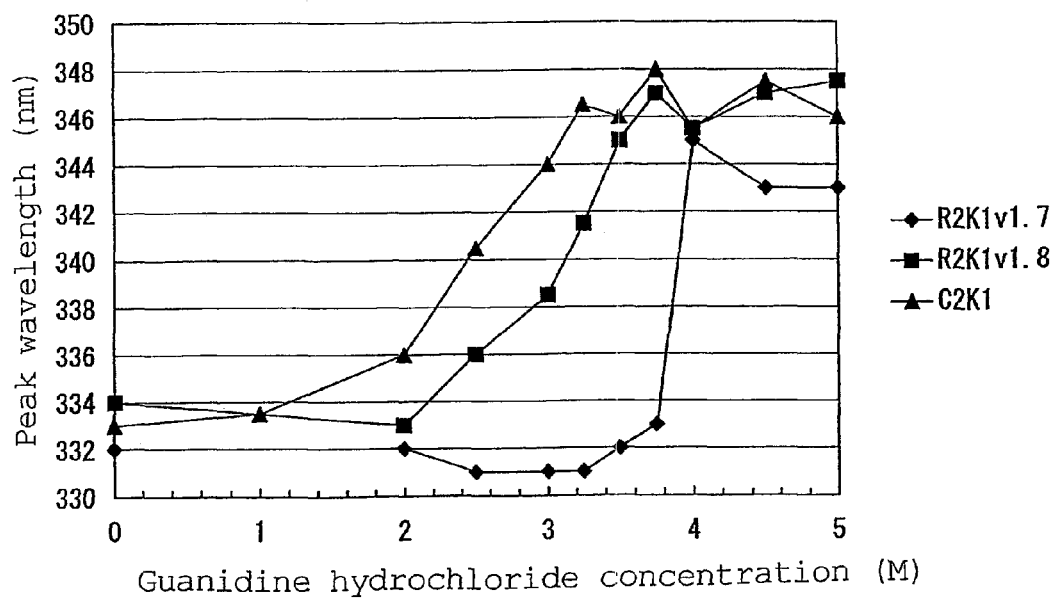
FIG. 8 shows the results of a plot of fluorescence spectral peak wavelengths of chimeric 2K1 antibody and humanized 2K1 antibody, treated with buffers containing various concentrations of guanidine hydrochloride.

Each of the C2K1 antibody and the two kinds of R2K1 antibody was adjusted to 50 µg/mL using a 20 mM sodium phosphate buffer+120 mM NaCl (pH 7) containing various concentrations of guanidine hydrochloride (for control, guanidine hydrochloride was not added), and allowed to stand at 10° C. overnight, after which the fluorescence spectrum of each sample was measured. The measurement of the fluorescence spectrum was performed using the FP-6500 Spectrofluorometer (JASCO Company). Using a cell having a light path length of 3 mm, the fluorescence emitted by tryptophan excited by 280 nm light was scanned over the wavelength range from 320 nm to 370 nm. The relationship between guanidine hydrochloride concentration and peak wavelength was compared among the antibodies. As a result, a shift of peak wavelength due to loosening of protein steric structure was observed from a time point where the guanidine hydrochloride concentration just exceeded 1 M for C2K1 or 2 M for R2K1v1.8, whereas the peak wavelength did not shift up to 3.8 M for R2K1v1.7 (FIG. 8). This demonstrated that the R2K1v1.7 antibody had improved resistance to guanidine hydrochloride compared to the R2K1v1.8 antibody and the C2K1 antibody.

(7. Evaluation of Low-pH Resistance by CD)

Each of the C2K1 antibody and the R2K1v1.7 antibody was adjusted to 2 mg/mL with 20 mM citrate buffer+120 mM NaCl (pH 6). 0.1 N HCl and distilled water were added thereto to prepare samples of various pH levels having an antibody concentration of 1 mg/mL; after being treated at room temperature for 1 hour, the CD spectrum of each sample was measured.

Figure 9:
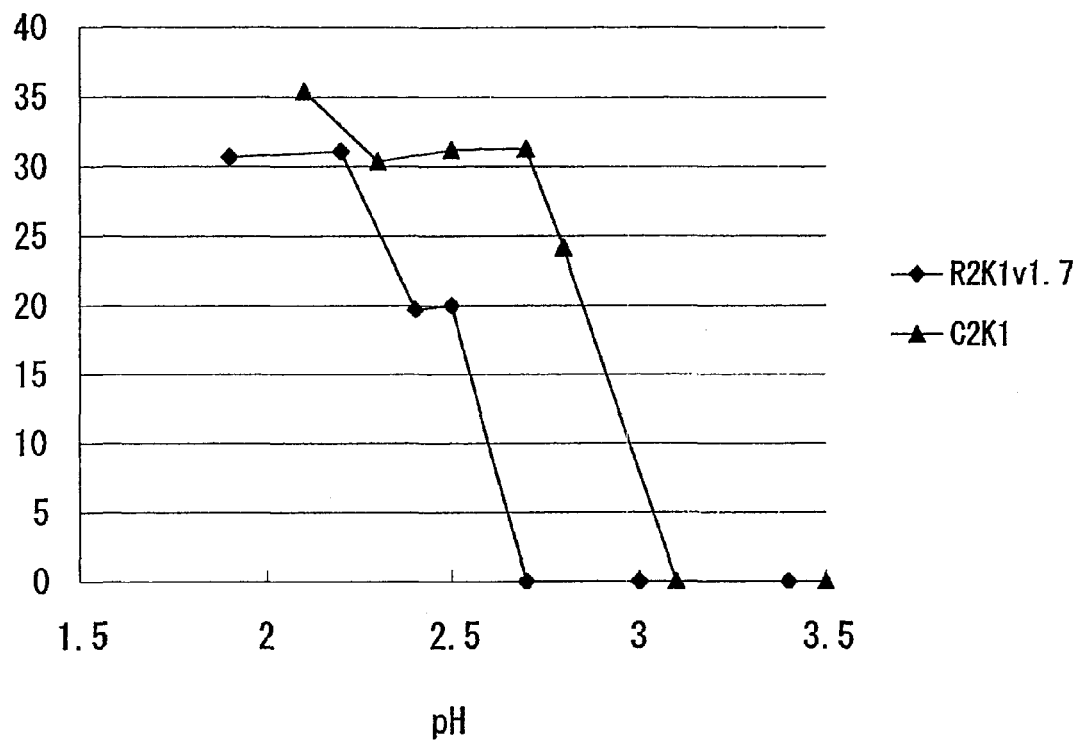
FIG. 9 shows the results of a measurement of the random structure contents in chimeric 2K1 antibody and humanized 2K1 antibody, treated with buffers at various pH levels, by CD.

Measurements of CD (circular dichroism) were performed using the J-820 Spectropolarimeter (JASCO Company). Using a cell having a light path length of 0.1 mm, the CD spectrum was measured over the wavelength range from 205 nm to 260 nm. The spectral analysis employed the JWSSE-480 model protein secondary structure analysis program (JASCO Company), which is based on the CD spectral analytical method of Yang et al. (Methods in Enzymology, 130, 208-269 (1986)). The relationship between random structure content ratio as calculated by this method and treatment pH was compared among the antibodies. As a result, the random structure content ratio increased from pH 3 for the C2K1 antibody, whereas no increase in random structure was observed up to pH 2.7 for R2K1v1.7 (FIG. 9). This confirmed that the R2K1v1.7 antibody had a resistance to a pH level lower by 0.3 than that of the C2K1 antibody.

(8. Evaluation of Heat Stability Using Differential Scanning Calorimeter)

Figure 10:
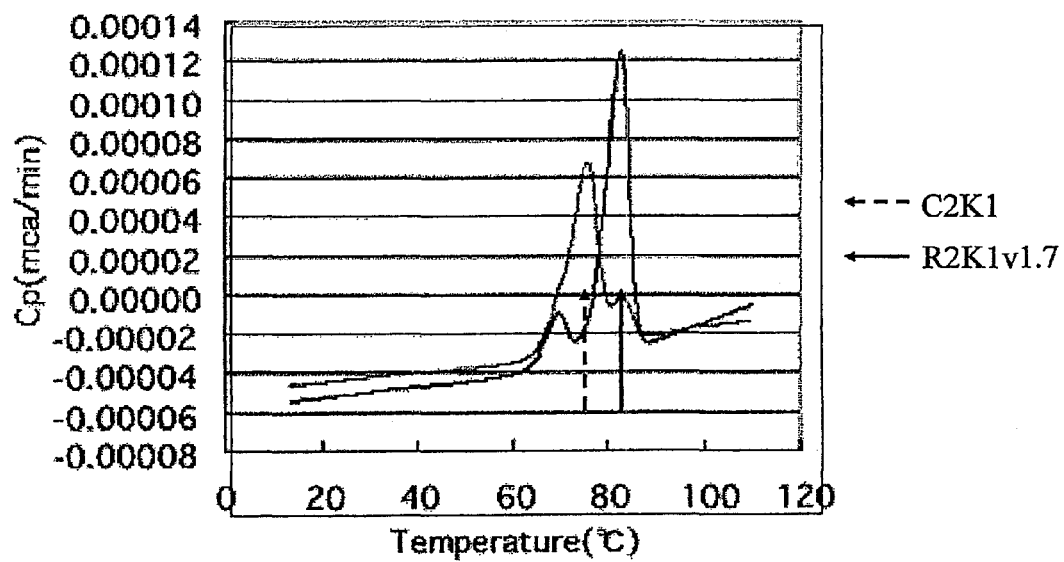
FIG. 10 is an illustration showing the results of an examination of the heat stability of chimeric 2K1 antibody and humanized 2K1 antibody using an ultra-sensitive differential scanning calorimeter. The dotted arrow and solid arrow indicate the Tm of chimeric 2K1 antibody and R2K1v1.7 antibody, respectively.

Each of the C2K1 antibody and the R2K1v1.7 antibody was dissolved in 20 mM citrate buffer+120 mM NaCl (pH 6.0) buffer at a concentration of 1 mg/mL, and its heat stability was examined using a MicroCal Company ultra-sensitive differential scanning calorimeter (VP capillary DSC platform). The results are shown in FIG. 10. The midpoint transition temperature (Tm), which indicates the higher structure denaturation temperature, was 76.0° C. for the C2K1 antibody and 82.8° C. for the R2K1v1.7 antibody; an increase of about 6° C. was confirmed. This demonstrated that the R2K1v1.7 antibody had remarkably improved heat stability.

(9. Cell Adhesion Inhibitory Effect of R2K1v1.7 on OPN)

To compare the pharmacological effects of the R2K1v1.7 of the present invention of this application and a commonly known humanized anti-OPN antibody (see WO03/027151; hereinafter referred to as R2K1v0), the cell adhesion inhibitory effects of these two antibodies on human OPN were examined.

1. Culture and Passage of Cells

Jurkat E6.1 cells were purchased from Dainippon Pharmaceutical Co., Ltd., and passaged and cultured using RPMI1640 (10% FCS, penicillin-streptomycin).

2. Preparation of Reagents

Adhesion buffer (L-15 medium, 1% BSA, 50 mM HEPES, pH 7.4) PMA solution (40 ng/mL phorbol 12-myristate 13-acetate (PMA) [SIGMA] in adhesion buffer)

CV staining solution (0.5% Crystal Violet, 1% formamide, 20% methanol)

GST solution (5 µg/mL glutathione S-transferase (GST) [SIGMA] in PBS (−))

Human $IgG_1$ solution (400 µg/mL in PBS (−)) [CALBIOCHEM]

3. Preparation of Thrombin-Cleaved Human N-Terminal Osteopontin (OPN)

GST-fused thrombin-cleaved human N-terminal OPN (GST-human N-OPN, 1.6 mg/mL) was prepared as described in WO02/081522, and was used in the experiments after being diluted with PBS (−) to 5 µg/mL.

4. Preparation of Test Drugs

Each of R2K1v1.7 (18.6 mg/mL) and R2K1v0 (4.39 mg/mL) was diluted with PBS (−) to 4, 12, 40, 120, and 400 (µg/mL); human $IgG_1$ was added to all these diluted solutions to obtain a total protein concentration of 400 µg/mL.

5. Grouping

Blank Group (GST)

Control Group

Test drug group R2K1v1.7 (1, 3, 10, 30, 100 µg/mL)
R2K1v0 (1, 3, 10, 30, 100 µg/mL)

6. Cell Adhesion Experiments

To all wells, except blank wells, of a 96-well microplate, 25 µL of the GST-human N—OPN solution was added, or 25 µL of the GST solution was added for the blank group, and the plate was incubated at 37° C. for 1 hour, after which the plate was twice washed with PBS (−). 50 µL of the PMA solution was added, and the plate was incubated at 37° C. for 30 minutes, after which 25 µL of the test drug solution (test drug group) or the human $IgG_1$ solution (blank group and control group) was added. Jurkat E6.1 cells were suspended in the adhesion buffer to obtain a cell density of $2 \times 10^6$ cells/mL, and 25 µL was added all wells. The suspension was centrifuged at 15×g for 1 minute to precipitate the cells on the bottom of the plate, after which the plate was incubated at 37° C. for 1 hour. After completion of the reaction, the plate was inverted and centrifuged at 47×g for 2 minutes, and the supernatant (non-adhering cells) was removed. For quantitation of adhering cell count, 25 µL of the CV stain solution was added, the plate was allowed to stand at room temperature for 10 minutes to stain and fix the cells, after which the plate was washed with pure water three times, 25 µL of 1% Triton-X100 solution was added to all wells, and after solubilization of the cells was confirmed, absorbance (measuring wavelength 595 nm) was measured using a microplate reader (SPECTRAmax250, Molecular Devices).

7. Analysis

Figure 11:
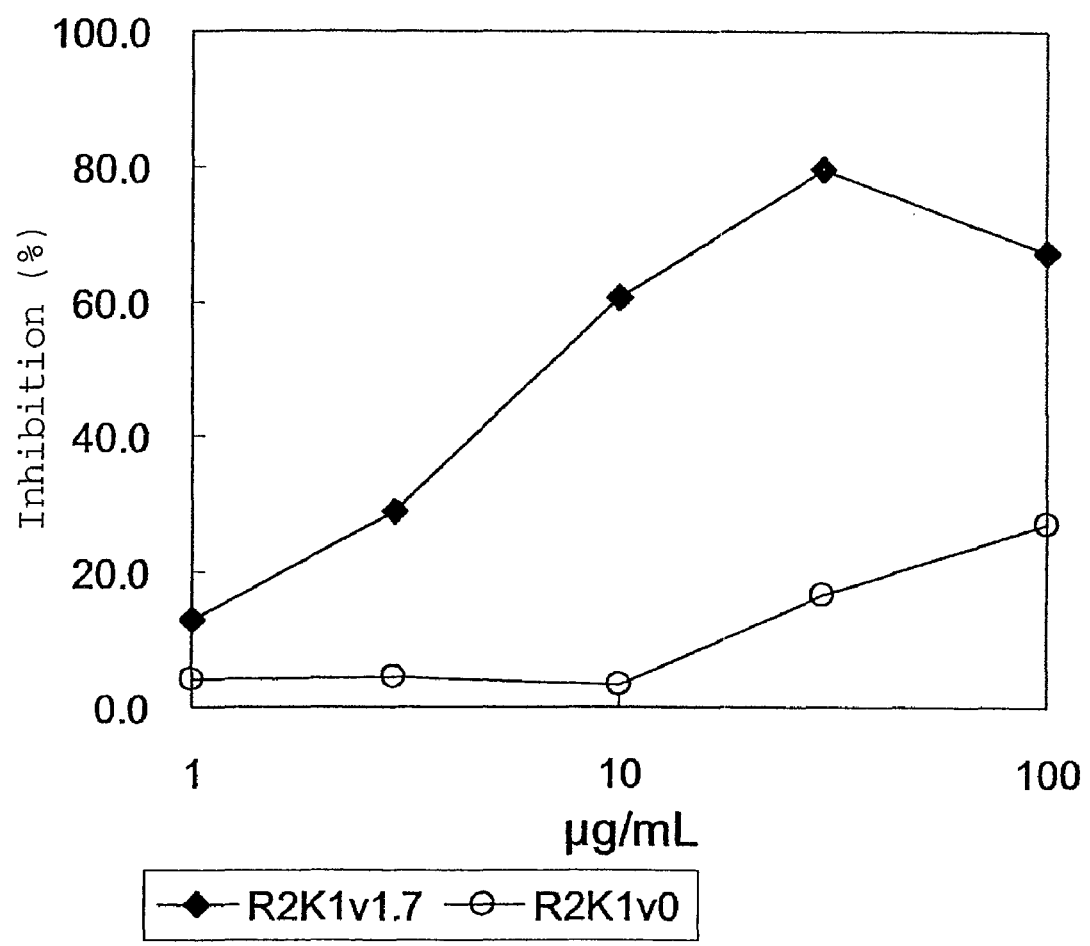
FIG. 11 shows the cell adhesion inhibitory effects of R2K1v1.7 and R2K1v0 on human OPN.

The experiments employed 5 wells per group. The mean value of absorbance and suppression rate for each group were calculated, and IC50 values (test drug concentrations for a suppression rate of 50%) were calculated. The suppression rate for the blank group was defined as 100% and that for the control group as 0%. The IC50 values were calculated by plotting logarithmic test drug concentration on the X-axis and suppression rate on the Y-axis, and applying the data to a linear regression equation by the least square method. The calculations of the IC50 values employed data obtained at test drug concentrations showing a linear dose-response relation. From the results shown in FIG. 11, it is understood that the cell adhesion inhibitory effect of a commonly known humanized anti-human OPN antibody is extremely low, whereas R2K1v1.7 has an excellent cell adhesion inhibitory effect (IC50 value: 6.4).

(10. Effects of R2K1v1.7 on Collagen-Induced Arthritis in Cynomolgus Monkey)

Bovine type II collagen (Collagen Gijyutsu Kenshukai) in emulsion in Freund's complete adjuvant (Becton Dickinson and Company) was immunized to the backs and tails of female cynomolgus monkeys 36 days before medication, and a booster was administered 15 days before medication. The animals were randomized into three medication-treated groups (n=10) on the basis of percent changes in body weight and proximal interphalangeal joint oblong area compared to pre-immunization levels. R2K1v1.7 or solvent control was given at a dose of 25 mg/kg or 50 mg/kg by intravenous injection once a week eight times in total. The first day of medication was defined as day 0. On days 0, 6, 13, 20, 27, 34, 41, 48 and 55 during the administration period, as a sign of joint swelling, proximal interphalangeal joint oblong area was monitored. The minor and major axes of the proximal interphalangeal joints of the anterior and posterior legs were measured using calipers, the oblong areas were calculated, and the mean value of the oblong areas of 16 fingers was used as the proximal interphalangeal joint oblong area. Percent changes in proximal interphalangeal joint oblong area were calculated relative to the pre-medication value as 100. On day 0, and on days 6, 13, 20, 27, 34, 41, 48 and 55 (6 days after medication), plasma was collected, and the R2K1v1.7 and the anti-R2K1v1.7 antibody were measured. This measured concentration of R2K1v1.7 in plasma corresponds to the trough level. Data analysis was performed after deleting the data on anti-R2K1v1.7 antibody-positive animals and animals that died during the study period.

Figure 12:
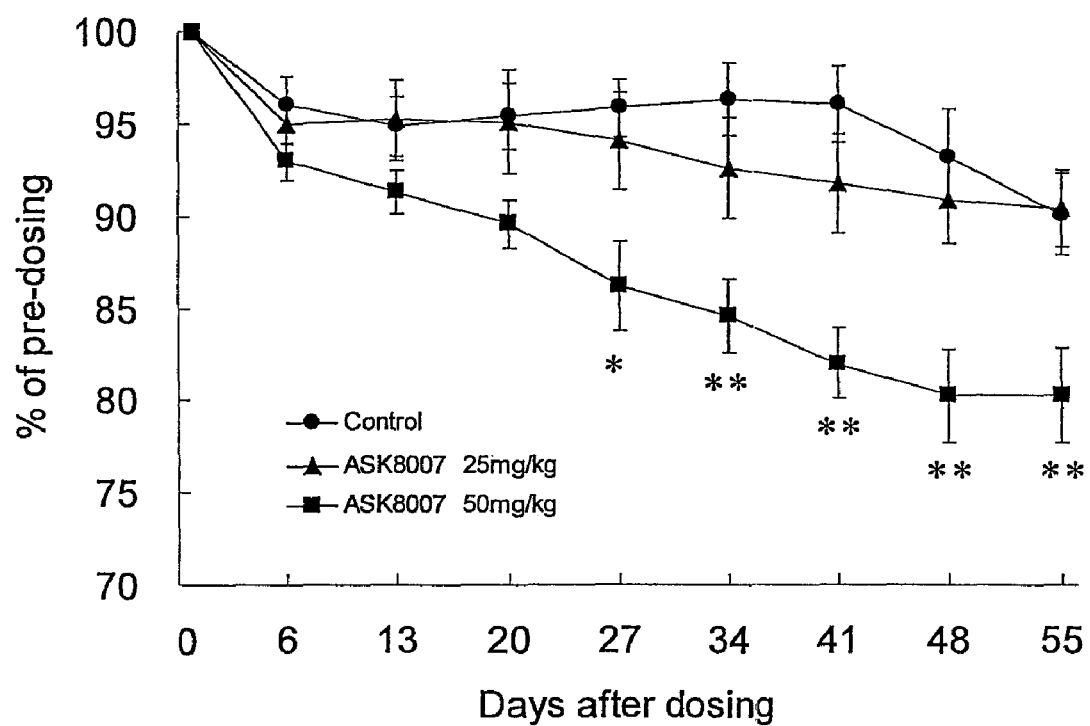
FIG. 12 shows the effects of R2K1v1.7 on joint swelling in monkey collagen-induced arthritis. The data are shown as mean±SE for 8 animals, 7 animals and 5 animals in the control group, 25 mg/kg group and 50 mg/kg group, respectively. $*p<0.05$, $**p<0.01$: significantly different from control group as determined by Dunnet's multiple comparison test.

In 1 animal in the 25 mg/kg dose R2K1v1.7 group and 4 animals in the 50 mg/kg dose R2K1v1.7 group, the anti-R2K1v1.7 antibody was generated. Two animals in the solvent control group, 2 animals in the 25 mg/kg dose R2K1v1.7 group, and 1 animal in the 50 mg/kg dose R2K1v1.7 group died after medication. The deceased cases were attributed to general weakening due to severe inflammation. The treatment with 50 mg/kg R2K1v1.7 significantly reduced foot swelling as measured by percent change in proximal interphalangeal joint oblong area compared to the control solvent group between day 27 and day 55 (FIG. 12). R2K1v1.7 at a dose of 25 mg/kg had no significant effect on the change in proximal interphalangeal joint oblong area. At doses of 25 mg/kg and 50 mg/kg, R2K1v1.7 trough concentrations in plasma were 38.41 to 76.13 µg/mL and 73.91 to 125.3 µg/mL, respectively. The SVVYGLR sequence of human OPN, unlike the corresponding sequence of monkey OPN (SVAYGLR) (SEQ ID NO:11), the binding affinity of R2K1v1.7 for this human OPN peptide is more than 100 times higher than the binding affinity for the corresponding monkey OPN peptide. With these findings in mind, the effective plasma concentration of R2K1v1.7 in the treatment of arthritis is estimated to be not more than 100 µg/mL.

(11. Preparation of scFv of R2K1v1.7)

By a PCR with the above-described heavy-chain expression plasmid having R2K1-VH1.7 and light-chain expression plasmid having R2K1-VL1.7 as the templates, a DNA fragment that encodes a single-stranded variable region fragment (scFv) having the structure of VH1.7-linker-VL1.7 (the linker was the base sequence that encodes the amino acid sequence shown by GGGGSGGGGSGGGGS (SEQ ID NO:14)) was prepared. Added at the end of this DNA fragment is a sequence recognized by the restriction endonucleases SfiI and NotI. This DNA fragment was digested with the restriction endonucleases SfiI and NotI, and inserted to the SfiI site and NotI site of the pCANTAB5E vector (Marks, J. D., et. al, J. Mol. Biol., vol. 222, p581-97, 1991), also previously digested with SfiI and NotI, whereby an R2K1-VH1.7 scFv expression plasmid was prepared. In this expression plasmid, a base sequence that encodes E-Tag is added downstream of the coding region of scFv. This plasmid was introduced to the *Escherichia coli* HB2151 strain according to a conventional 1 method, and sown to a SOBAG agar plate (an SOB plate containing 2% glucose and 100 µg/mL ampicillin) to yield a transformant clone. From the clone obtained, a plasmid DNA was extracted; the sequence of the coding region of scFv was confirmed by DNA base sequence analysis with the plasmid DNA as the template. The DNA base sequence analysis employed the DTCS-Quick Start Kit and the CEQ2000XL DNA Analysis System (both from Beckman Coulter, K.K.). The base sequence obtained is shown by SEQ ID NO:9.

After the *Escherichia coli* clone whose base sequence was confirmed was cultured using a 2xYT medium containing 2% glucose and 100 µg/mL ampicillin, a portion thereof was suspended in a 2xYT medium supplemented with 1 mM IPTG and 100 µg/mL ampicillin, and further cultured overnight to induce the expression of scFv. After completion of the cultivation, the cells were recovered by centrifugation, suspended in a PBS containing 1 mM EDTA, and allowed to stand in ice for 30 minutes. Next, the suspension was centrifuged at 10,000 rpm for 15 minutes, and the supernatant was recovered and filtered through a 0.45 µm filter, whereby a periplasm fraction containing scFv was obtained. The scFv of R2k1v1.7 (hereinafter referred to as R2K1v1.7-scFv) was purified from this periplasm fraction by affinity chromatography using anti-E-Tag antibody.

Figure 13:
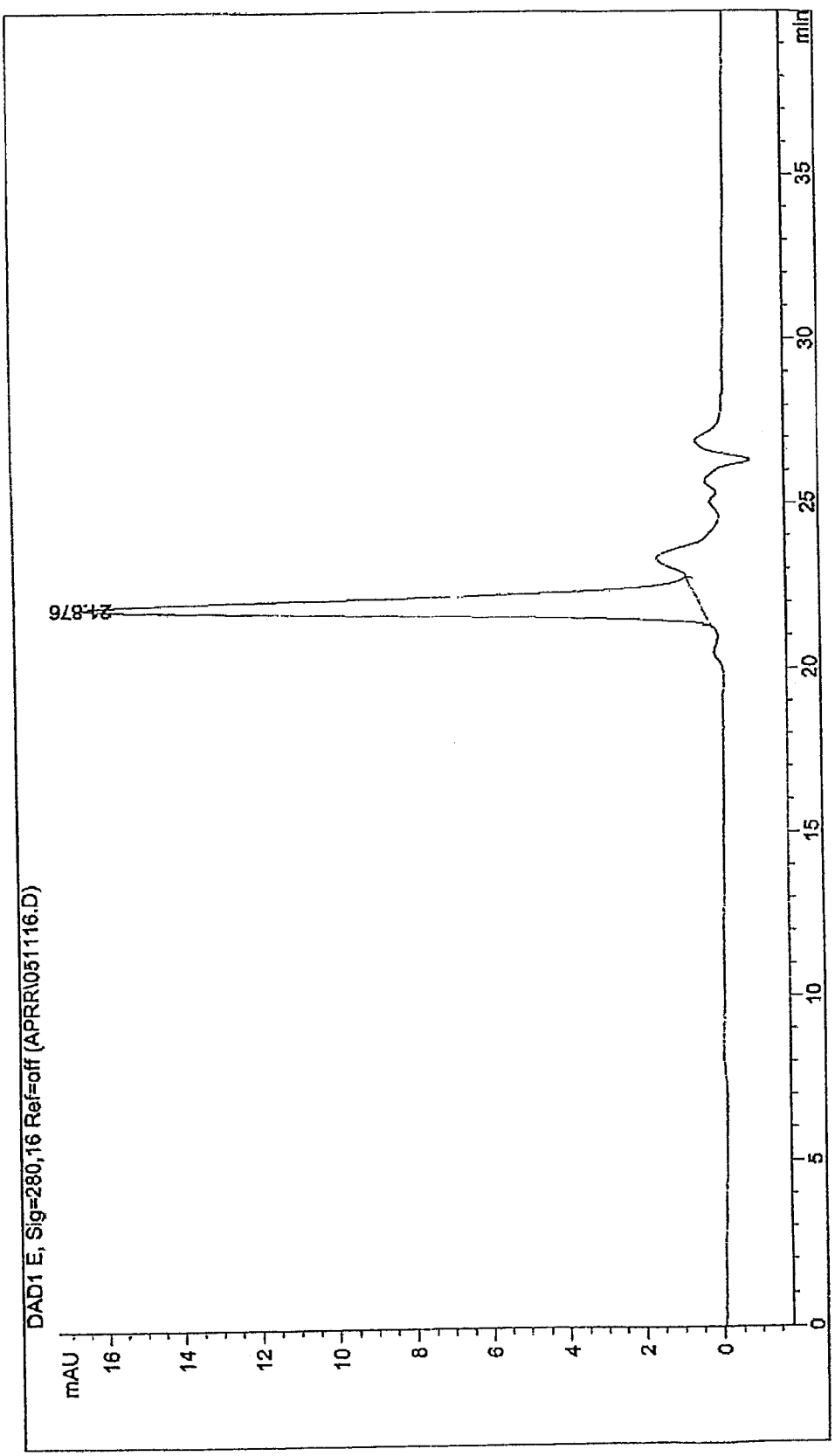
FIG. 13 shows the results of an analysis of purified R2K1v1.7-scFv by HPLC.

The R2K1v1.7-scFv thus prepared was subjected to gel filtration chromatography; from the separation pattern shown in FIG. 13, it was confirmed that nearly all was monomeric.

(12. Confirmation of Bindability of R2K1v1.7-scFv to Human Osteopontin Peptide)

Figure 14:
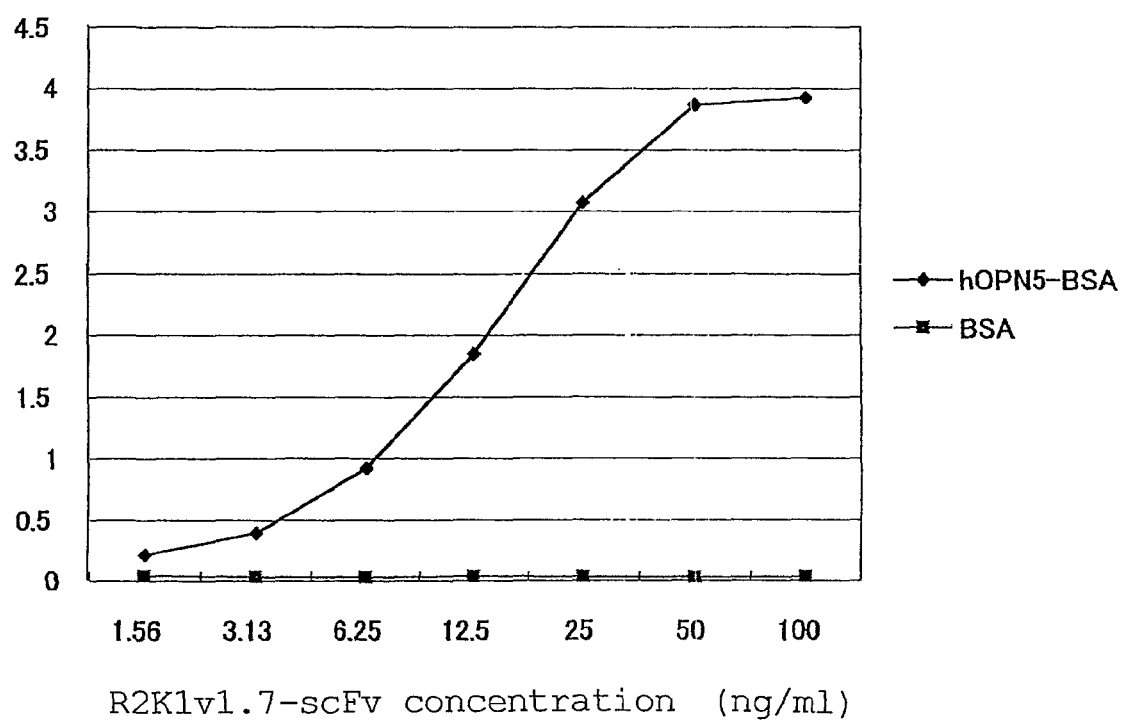
FIG. 14 shows the results of an examination of the bindability of purified R2K1v1.7-scFv to the hOPN5 peptide by an ELISA method.

The binding activity of the purified R2K1v1.7-scFv to the hOPN5 peptide was measured by an ELISA method. The method was generally the same as described above; in this measurement, HRP-labeled anti-E-Tag antibody was used as the labeled antibody. The results are shown in FIG. 14. It was confirmed that the purified R2K1v1.7-scFv did not bind to the negative control BSA but bound specifically to the hOPN5 peptide.

(13. Preparation of Polyethylene Glycol Modified Antibody Fragment)

Figure 15:
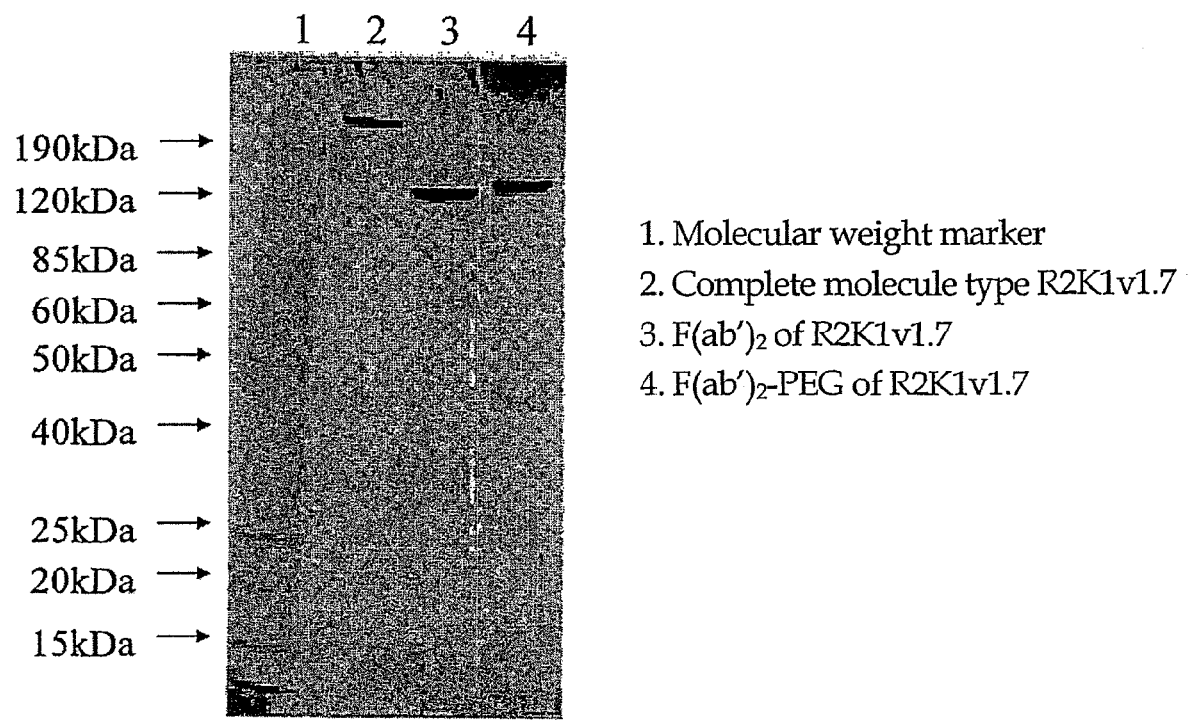
FIG. 15 shows the results of SDS-PAGE of the complete molecule type R2K1v1.7 antibody and the F (ab')$_2$ and purified F (ab')$_2$—PEG of the R2K1v1.7 antibody.

After the R2K1v1.7 antibody was pepsinized by a standard method, purified F(ab')$_2$ was obtained using a Protein G HP column (both from Amersham Biosciences K.K.) and a Hi prep 16/60 Sephacryl S-200 High Resolution column (Amersham Biosciences K.K.). Subsequently, the purified F(ab')$_2$ was reduced with 0.1 M DTT to activate the thiol group, after which gel filtration using a Sephadex G-25 column (Amersham Biosciences K.K.) was performed to remove the DTT. The Fab' thus obtained was mixed with maleimidated polyethylene glycol SUNBRIGHT ME-120MA (NOF Corporation) in a molar ratio of 1:10, and allowed to stand at 4° C. overnight to cause a coupling reaction. After iodoacetamide (Nacalai Tesque) was added to stop the coupling reaction, a polyethylene glycol modified F(ab')$_2$ (hereinafter also referred to as F(ab')$_2$—PEG) was obtained by gel filtration using a Hi prep 16/60 Sephacryl S-200 High Resolution column. The results of SDS-PAGE are shown in FIG. 15. By a comparison with unmodified F(ab')$_2$ electrophoresed for reference control, an increase in the molecular weight by the polyethylene glycol modification was confirmed.

(14. Confirmation of Binding Activity of F(ab')$_2$—PEG to Osteopontin Peptide)

Figure 16:
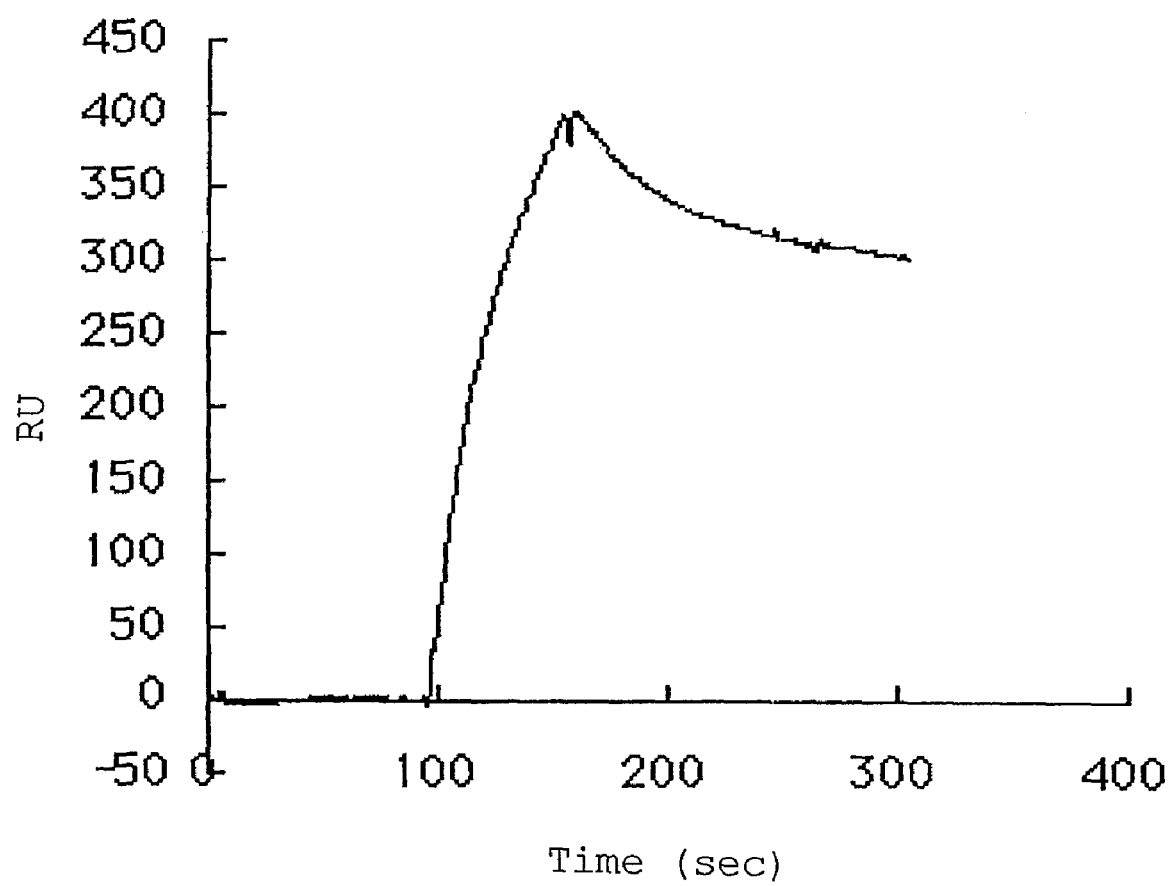
FIG. 16 shows the results of an examination of the bindability of the F (ab')$_2$—PEG of R2K1v1.7 to the hOPN5 peptide by BIAcore.

The binding activity of the purified F(ab')$_2$—PEG of R2K1v1.7 to the hOPN5 peptide was confirmed using surface plasmon resonance assay. The biotinized hOPN5 peptide was immobilized on Sensor Chip SA (BIAcore Company), and its binding activity was confirmed using the F(ab')$_2$—PEG, previously diluted to 5 µg/mL with HBS-EP buffer (BIAcore Company); the results are shown in FIG. 16. From a rise in the signal, this F(ab')$_2$—PEG was confirmed as having the same binding activity to the hOPN5 peptide as that of R2K1v1.7.

Because the humanized anti-human osteopontin antibody of the present invention is excellent in both activities (antigen binding activity, leukocyte migration inhibitory activity and the like) and/or stability (resistance to heat, low-pH conditions, denaturants and the like), it is useful as a more effective drug than conventional anti-human osteopontin antibodies in the prevention or treatment of various inflammatory diseases, including autoimmune disease, rheumatism, rheumatoid arthritis, and osteoarthritis.

The cell line Sp2/0-R2K1v1.7, which produces the R2K1v1.7 monoclonal antibody was deposited under deposit number FERM BP-10821 under the terms of the Budapest Treaty at the International Patent Organism Depository, National Institute of Advanced Industrial Science and Technology, AIST Tsukuba Central 6, 1-1, Higashi 1-Chome Tsukuba-shi, Ibaraki-ken 30508566.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

This application is based on patent application No. 2006-152892 filed in Japan, and the contents disclosed therein are hereby entirely incorporated by reference. In addition, the contents disclosed in any publication cited herein, including patents and patent applications, are hereby incorporated in their entireties by reference, to the extent that they have been disclosed herein.

The invention claimed is:

1. A humanized anti-human osteopontin antibody comprising:
- a heavy-chain variable region consisting of the amino acid sequence shown by SEQ ID NO: 1 and
- a light-chain variable region consisting of the amino acid sequence shown by SEQ ID NO: 3; or
- a human osteopontin-binding fragment of said humanized anti-human osteopontin antibody.

2. The humanized anti-human osteopontin antibody of claim 1, wherein the heavy-chain constant region of the antibody is human Ig$_\gamma$1.

3. The humanized anti-human osteopontin antibody of claim 1, wherein the light-chain constant region of the antibody is human Ig$_\kappa$.

4. The humanized anti-human osteopontin antibody of claim 1, wherein the heavy-chain constant region of the antibody is human Ig$_\gamma$1 and the light-chain constant region of the antibody is human Ig$_\kappa$.

5. The humanized anti-human osteopontin antibody of claim 1, which comprises a heavy chain consisting of the amino acid sequence shown by SEQ ID NO: 25 and a light chain consisting of the amino acid sequence shown by SEQ ID NO: 27.

6. A therapeutic drug for rheumatoid arthritis comprising the humanized anti-human osteopontin antibody of any one of claims 1 to 5.

7. A composition comprising the humanized anti-human osteopontin antibody of claim 1 and a pharmaceutically acceptable carrier or additive.

8. A fragment of the antibody of claim 1 that binds to human osteopontin.

9. The fragment of claim 8, which is an Fab, Fab', or F(ab')$_2$ fragment.

10. The humanized anti-human osteopontin antibody of claim 1 which is R2K1v1.7 produced by cell line Sp2/0-R2K1v1.7 deposited under deposit number FERM BP-10821, or an human osteopontin-binding fragment thereof.

11. A method for treating rheumatoid arthritis comprising administering to a human subject in need thereof the humanized anti-human osteopontin antibody of claim 1.

12. The method of claim 11, wherein said antibody is administered intravenously.

13. The method of claim 11, wherein said antibody is administered subcutaneously.

* * * * *

SEQUENCE LISTING

<160> NUMBER OF SEQ ID NOS: 27

<210> SEQ ID NO 1
<211> LENGTH: 116
<212> TYPE: PRT
<213> ORGANISM: Artificial
<220> FEATURE:

<223> OTHER INFORMATION: Synthetic Construct

<400> SEQUENCE: 1

```
Gln Val Gln Leu Gln Gln Ser Gly Ala Glu Val Lys Lys Pro Gly Ala
1               5                   10                  15

Ser Val Lys Val Ser Cys Lys Ala Leu Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile His Pro Gly Arg Gly Gly Thr Ala Tyr Asn Gln Lys Phe
    50                  55                  60

Lys Gly Lys Ala Thr Leu Thr Ala Asp Lys Ser Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Ile Thr Gly Tyr Phe Asp Val Trp Gly Gln Gly Thr Thr Val
            100                 105                 110

Thr Val Ser Ser
        115
```

<210> SEQ ID NO 2
<211> LENGTH: 116
<212> TYPE: PRT
<213> ORGANISM: Artificial
<220> FEATURE:
<223> OTHER INFORMATION: Synthetic Construct

<400> SEQUENCE: 2

```
Gln Val Gln Leu Val Gln Ser Gly Ala Glu Leu Val Arg Pro Gly Ser
1               5                   10                  15

Ser Val Lys Val Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile His Pro Gly Arg Gly Gly Thr Ala Tyr Asn Gln Lys Phe
    50                  55                  60

Lys Gly Lys Ala Thr Leu Thr Ala Asp Lys Ser Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Ile Thr Gly Tyr Phe Asp Val Trp Gly Gln Gly Thr Thr Val
            100                 105                 110

Thr Val Ser Ser
        115
```

<210> SEQ ID NO 3
<211> LENGTH: 113
<212> TYPE: PRT
<213> ORGANISM: Artificial
<220> FEATURE:
<223> OTHER INFORMATION: Synthetic Construct

<400> SEQUENCE: 3

```
Asp Val Val Met Thr Gln Ser Pro Leu Ser Leu Ser Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
```

-continued

```
                 35                  40                  45
Pro Gln Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gln Gly Thr Lys Leu Glu Ile Lys
                100                 105                 110

Arg

<210> SEQ ID NO 4
<211> LENGTH: 113
<212> TYPE: PRT
<213> ORGANISM: Artificial
<220> FEATURE:
<223> OTHER INFORMATION: Synthetic Construct

<400> SEQUENCE: 4

Asp Val Val Met Thr Gln Ser Pro Leu Ser Leu Pro Val Thr Leu Gly
1               5                  10                  15

Gln Pro Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Gln Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gln Gly Thr Lys Leu Glu Ile Lys
                100                 105                 110

Arg

<210> SEQ ID NO 5
<211> LENGTH: 348
<212> TYPE: DNA
<213> ORGANISM: Artificial
<220> FEATURE:
<223> OTHER INFORMATION: R2K1-VH1.7 region
<220> FEATURE:
<221> NAME/KEY: CDS
<222> LOCATION: (1)..(348)

<400> SEQUENCE: 5 cag gtg cag ctg cag cag tct ggg gct gag gtg aag aag cct ggg gcc      48
Gln Val Gln Leu Gln Gln Ser Gly Ala Glu Val Lys Lys Pro Gly Ala
1               5                  10                  15 tcc gtg aag gtc tcc tgc aag gct ttg ggg tat acc ttc act gac tat      96
Ser Val Lys Val Ser Cys Lys Ala Leu Gly Tyr Thr Phe Thr Asp Tyr
                 20                  25                  30 gaa atg cac tgg gtg aag cag acc cct gta cat ggg ctt gag tgg att     144
Glu Met His Trp Val Lys Gln Thr Pro Val His Gly Leu Glu Trp Ile
             35                  40                  45 gga gct att cat cca gga aga ggt ggt act gcc tac aat cag aag ttc     192
Gly Ala Ile His Pro Gly Arg Gly Gly Thr Ala Tyr Asn Gln Lys Phe
         50                  55                  60 aag ggc aag gcc acg ctg acc gcg gac aaa tcc act agt aca gcc tac     240
```

```
Lys Gly Lys Ala Thr Leu Thr Ala Asp Lys Ser Thr Ser Thr Ala Tyr
 65                  70                  75                  80 atg gag ctg agc agc ctg aca tct gag gac acg gcc gtg tat tac tgt    288
Met Glu Leu Ser Ser Leu Thr Ser Glu Asp Thr Ala Val Tyr Tyr Cys
                 85                  90                  95 aca aga att act ggg tac ttc gat gtc tgg ggg caa ggg acc acg gtc    336
Thr Arg Ile Thr Gly Tyr Phe Asp Val Trp Gly Gln Gly Thr Thr Val
            100                 105                 110 acc gtc tcc tca                                                    348
Thr Val Ser Ser
        115

<210> SEQ ID NO 6
<211> LENGTH: 348
<212> TYPE: DNA
<213> ORGANISM: Artificial
<220> FEATURE:
<223> OTHER INFORMATION: R2K1-VH1.8 region
<220> FEATURE:
<221> NAME/KEY: CDS
<222> LOCATION: (1)..(348)

<400> SEQUENCE: 6 cag gtg cag ctg gtg cag tct ggg gct gag ctg gtg agg cct ggg tcc     48
Gln Val Gln Leu Val Gln Ser Gly Ala Glu Leu Val Arg Pro Gly Ser
 1               5                  10                  15 tcc gtg aag gtc tcc tgc aag gct tct ggg tat acc ttc act gac tat     96
Ser Val Lys Val Ser Cys Lys Ala Ser Gly Tyr Thr Phe Thr Asp Tyr
                20                  25                  30 gaa atg cac tgg gtg aag cag acc cct gta cat ggg ctt gag tgg att    144
Glu Met His Trp Val Lys Gln Thr Pro Val His Gly Leu Glu Trp Ile
            35                  40                  45 gga gct att cat cca gga aga ggt ggt act gcc tac aat cag aag ttc    192
Gly Ala Ile His Pro Gly Arg Gly Gly Thr Ala Tyr Asn Gln Lys Phe
 50                  55                  60 aag ggc aag gcc acg ctg acc gcg gac aaa tcc act agt aca gcc tac    240
Lys Gly Lys Ala Thr Leu Thr Ala Asp Lys Ser Thr Ser Thr Ala Tyr
 65                  70                  75                  80 atg gag ctg agc agc ctg aca tct gag gac acg gcc gtg tat tac tgt    288
Met Glu Leu Ser Ser Leu Thr Ser Glu Asp Thr Ala Val Tyr Tyr Cys
                 85                  90                  95 aca aga att act ggg tac ttc gat gtc tgg ggg caa ggg acc acg gtc    336
Thr Arg Ile Thr Gly Tyr Phe Asp Val Trp Gly Gln Gly Thr Thr Val
            100                 105                 110 acc gtc tcc tca                                                    348
Thr Val Ser Ser
        115

<210> SEQ ID NO 7
<211> LENGTH: 339
<212> TYPE: DNA
<213> ORGANISM: Artificial
<220> FEATURE:
<223> OTHER INFORMATION: R2K1-VL1.7 region
<220> FEATURE:
<221> NAME/KEY: CDS
<222> LOCATION: (1)..(339)

<400> SEQUENCE: 7 gat gtt gtg atg act cag tct cca ctc tcc ctg agc gtc acc ctt gga     48
Asp Val Val Met Thr Gln Ser Pro Leu Ser Leu Ser Val Thr Leu Gly
 1               5                  10                  15 cag ccg gcc tcc atc tcc tgc agg agc tct caa agc att gta cat agt     96
Gln Pro Ala Ser Ile Ser Cys Arg Ser Ser Gln Ser Ile Val His Ser
```

|  |  |  |  |  |  |  |  |  |  |  |  |  |  |  |  | |
|---|---|---|---|---|---|---|---|---|---|---|---|---|---|---|---|---|
|  |  |  | 20 |  |  |  | 25 |  |  |  | 30 |  |  |  |  | |

```
aat gga aac acc tat ttg gaa tgg tac ctg cag aag cca ggg cag tct      144
Asn Gly Asn Thr Tyr Leu Glu Trp Tyr Leu Gln Lys Pro Gly Gln Ser
         35                  40                  45 cca cag ctc ctg atc tat aaa gtt tcc aac cga ttt tct ggg gtc cca      192
Pro Gln Leu Leu Ile Tyr Lys Val Ser Asn Arg Phe Ser Gly Val Pro
 50                  55                  60 gac aga ttc agc ggc agt ggg tca ggc act gat ttc aca ctg aaa atc      240
Asp Arg Phe Ser Gly Ser Gly Ser Gly Thr Asp Phe Thr Leu Lys Ile
65                  70                  75                  80 agc agg gtt gaa gct gaa gac gtc gga gtt tat tac tgc ttt caa ggt      288
Ser Arg Val Glu Ala Glu Asp Val Gly Val Tyr Tyr Cys Phe Gln Gly
                 85                  90                  95 tca cat gtt ccg ctc acg ttt ggc cag ggg acc aag ctg gag atc aaa      336
Ser His Val Pro Leu Thr Phe Gly Gln Gly Thr Lys Leu Glu Ile Lys
            100                 105                 110 cgt                                                                  339
Arg

<210> SEQ ID NO 8
<211> LENGTH: 339
<212> TYPE: DNA
<213> ORGANISM: Artificial
<220> FEATURE:
<223> OTHER INFORMATION: R2K1-VL1.8 region
<220> FEATURE:
<221> NAME/KEY: CDS
<222> LOCATION: (1)..(339)

<400> SEQUENCE: 8 gat gtt gtg atg act cag tct cca ctc tcc ctg ccc gtc acc ctt gga      48
Asp Val Val Met Thr Gln Ser Pro Leu Ser Leu Pro Val Thr Leu Gly
1               5                   10                  15 cag ccg gcc tcc atc tcc tgc agg agc tct caa agc att gta cat agt      96
Gln Pro Ala Ser Ile Ser Cys Arg Ser Ser Gln Ser Ile Val His Ser
             20                  25                  30 aat gga aac acc tat ttg gaa tgg tac ctg cag aag cca ggg cag tct     144
Asn Gly Asn Thr Tyr Leu Glu Trp Tyr Leu Gln Lys Pro Gly Gln Ser
         35                  40                  45 cca cag ctc ctg atc tat aaa gtt tcc aac cga ttt tct ggg gtc cca     192
Pro Gln Leu Leu Ile Tyr Lys Val Ser Asn Arg Phe Ser Gly Val Pro
 50                  55                  60 gac aga ttc agc ggc agt ggg tca ggc act gat ttc aca ctg aaa atc     240
Asp Arg Phe Ser Gly Ser Gly Ser Gly Thr Asp Phe Thr Leu Lys Ile
65                  70                  75                  80 agc agg gtt gaa gct gaa gac gtc gga gtt tat tac tgc ttt caa ggt     288
Ser Arg Val Glu Ala Glu Asp Val Gly Val Tyr Tyr Cys Phe Gln Gly
                 85                  90                  95 tca cat gtt ccg ctc acg ttt ggc cag ggg acc aag ctg gag atc aaa     336
Ser His Val Pro Leu Thr Phe Gly Gln Gly Thr Lys Leu Glu Ile Lys
            100                 105                 110 cgt                                                                 339
Arg

<210> SEQ ID NO 9
<211> LENGTH: 732
<212> TYPE: DNA
<213> ORGANISM: Artificial
<220> FEATURE:
<223> OTHER INFORMATION: R2K1v1.7-scFv

<400> SEQUENCE: 9
```

```
caggtgcagc tgcagcagtc tggggctgag gtgaagaagc ctgggcctc cgtgaaggtc      60 tcctgcaagg ctttgggta taccttcact gactatgaaa tgcactgggt gaagcagacc     120
cctgtacatg gcttgagtg gattggagct attcatccag gaagaggtgg tactgcctac     180
aatcagaagt tcaagggcaa ggccacgctg accgcggaca atccactag tacagcctac     240 atggagctga gcagcctgac atctgaggac acggccgtgt attactgtac aagaattact     300
gggtacttcg atgtctgggg gcaagggacc acggtcaccg tctcctcagg tggaggcggt     360
tcaggcggag gtggctctgg cggtggcgga tcggatgttg tgatgaccca gtctccactc     420
tccctgagcg tcacccttgg acagccggcc tccatctcct gcaggagctc tcaaagcatt     480
gtacatagta atggaaacac ctatttggaa tggtacctgc agaagccagg gcagtctcca     540
cagctcctga tctataaagt ttccaaccga ttttctgggg tcccagacag attcagcggc     600
agtgggtcag gcactgattt cacactgaaa atcagcaggg ttgaagctga agacgtcgga     660
gtttattact gctttcaagg ttcacatgtt ccgctcacgt ttggccaggg gaccaagctg     720
gagatcaaac gt                                                        732
```

```
<210> SEQ ID NO 10
<211> LENGTH: 7
<212> TYPE: PRT
<213> ORGANISM: Artificial
<220> FEATURE:
<223> OTHER INFORMATION: Partial peptide of human or pig osteopontin

<400> SEQUENCE: 10

Ser Val Val Tyr Gly Leu Arg
1               5

<210> SEQ ID NO 11
<211> LENGTH: 7
<212> TYPE: PRT
<213> ORGANISM: Artificial
<220> FEATURE:
<223> OTHER INFORMATION: Partial peptide of monkey osteopontin

<400> SEQUENCE: 11

Ser Val Ala Tyr Gly Leu Arg
1               5

<210> SEQ ID NO 12
<211> LENGTH: 7
<212> TYPE: PRT
<213> ORGANISM: Artificial
<220> FEATURE:
<223> OTHER INFORMATION: Partial peptide of mouse or rat osteopontin

<400> SEQUENCE: 12

Ser Leu Ala Tyr Gly Leu Arg
1               5

<210> SEQ ID NO 13
<211> LENGTH: 18
<212> TYPE: PRT
<213> ORGANISM: Artificial
<220> FEATURE:
<223> OTHER INFORMATION: Partial peptide of osteopontin

<400> SEQUENCE: 13

Cys Val Asp Thr Tyr Asp Gly Arg Gly Asp Ser Val Val Tyr Gly Leu
1               5                   10                  15

Arg Ser
```

<210> SEQ ID NO 14
<211> LENGTH: 15
<212> TYPE: PRT
<213> ORGANISM: Artificial
<220> FEATURE:
<223> OTHER INFORMATION: Linker

<400> SEQUENCE: 14

Gly Gly Gly Gly Ser Gly Gly Gly Gly Ser Gly Gly Gly Gly Ser
1               5                  10                  15

<210> SEQ ID NO 15
<211> LENGTH: 441
<212> TYPE: DNA
<213> ORGANISM: Artificial
<220> FEATURE:
<223> OTHER INFORMATION: R2K1-VH1.7 depicted in Fig.1
<220> FEATURE:
<221> NAME/KEY: CDS
<222> LOCATION: (20)..(424)

<400> SEQUENCE: 15
cagcaagctt gccgccacc atg gaa tgg agc tgg atc ttt ctc ttc ctc ctg         52
                    Met Glu Trp Ser Trp Ile Phe Leu Phe Leu Leu
                     1               5                  10 tca gta act gca ggt gtc caa tcc cag gtg cag ctg cag cag tct ggg         100
Ser Val Thr Ala Gly Val Gln Ser Gln Val Gln Leu Gln Gln Ser Gly
             15                  20                  25 gct gag gtg aag aag cct ggg gcc tcc gtg aag gtc tcc tgc aag gct         148
Ala Glu Val Lys Lys Pro Gly Ala Ser Val Lys Val Ser Cys Lys Ala
         30                  35                  40 ttg ggg tat acc ttc act gac tat gaa atg cac tgg gtg aag cag acc         196
Leu Gly Tyr Thr Phe Thr Asp Tyr Glu Met His Trp Val Lys Gln Thr
     45                  50                  55 cct gta cat ggg ctt gag tgg att gga gct att cat cca gga aga ggt         244
Pro Val His Gly Leu Glu Trp Ile Gly Ala Ile His Pro Gly Arg Gly
 60                  65                  70                  75 ggt act gcc tac aat cag aag ttc aag ggc aag gcc acg ctg acc gcg         292
Gly Thr Ala Tyr Asn Gln Lys Phe Lys Gly Lys Ala Thr Leu Thr Ala
                 80                  85                  90 gac aaa tcc act agt aca gcc tac atg gag ctg agc agc ctg aca tct         340
Asp Lys Ser Thr Ser Thr Ala Tyr Met Glu Leu Ser Ser Leu Thr Ser
             95                  100                 105 gag gac acg gcc gtg tat tac tgt aca aga att act ggg tac ttc gat         388
Glu Asp Thr Ala Val Tyr Tyr Cys Thr Arg Ile Thr Gly Tyr Phe Asp
         110                 115                 120 gtc tgg ggg caa ggg acc acg gtc acc gtc tcc tca ggtgagtgga             434
Val Trp Gly Gln Gly Thr Thr Val Thr Val Ser Ser
     125                 130                 135 tccgcga                                                                  441

<210> SEQ ID NO 16
<211> LENGTH: 135
<212> TYPE: PRT
<213> ORGANISM: Artificial
<220> FEATURE:
<223> OTHER INFORMATION: Synthetic Construct

<400> SEQUENCE: 16

Met Glu Trp Ser Trp Ile Phe Leu Phe Leu Leu Ser Val Thr Ala Gly
1               5                   10                  15

Val Gln Ser Gln Val Gln Leu Gln Gln Ser Gly Ala Glu Val Lys Lys

-continued

```
                    20                  25                  30
Pro Gly Ala Ser Val Lys Val Ser Cys Lys Ala Leu Gly Tyr Thr Phe
            35                  40                  45

Thr Asp Tyr Glu Met His Trp Val Lys Gln Thr Pro Val His Gly Leu
 50                  55                  60

Glu Trp Ile Gly Ala Ile His Pro Gly Arg Gly Thr Ala Tyr Asn
 65                  70                  75                  80

Gln Lys Phe Lys Gly Lys Ala Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Ile Thr Gly Tyr Phe Asp Val Trp Gly Gln Gly
        115                 120                 125

Thr Thr Val Thr Val Ser Ser
    130                 135
```

<210> SEQ ID NO 17
<211> LENGTH: 441
<212> TYPE: DNA
<213> ORGANISM: Artificial
<220> FEATURE:
<223> OTHER INFORMATION: R2K1-VH1.8 depicted in Fig.2
<220> FEATURE:
<221> NAME/KEY: CDS
<222> LOCATION: (20)..(424)

<400> SEQUENCE: 17

```
cagcaagctt gccgccacc atg gaa tgg agc tgg atc ttt ctc ttc ctc ctg    52
                    Met Glu Trp Ser Trp Ile Phe Leu Phe Leu Leu
                      1               5                  10 tca gta act gca ggt gtc caa tcc cag gtg cag ctg gtg cag tct ggg    100
Ser Val Thr Ala Gly Val Gln Ser Gln Val Gln Leu Val Gln Ser Gly
            15                  20                  25 gct gag ctg gtg agg cct ggg tcc tcc gtg aag gtc tcc tgc aag gct    148
Ala Glu Leu Val Arg Pro Gly Ser Ser Val Lys Val Ser Cys Lys Ala
        30                  35                  40 tct ggg tat acc ttc act gac tat gaa atg cac tgg gtg aag cag acc    196
Ser Gly Tyr Thr Phe Thr Asp Tyr Glu Met His Trp Val Lys Gln Thr
    45                  50                  55 cct gta cat ggg ctt gag tgg att gga gct att cat cca gga aga ggt    244
Pro Val His Gly Leu Glu Trp Ile Gly Ala Ile His Pro Gly Arg Gly
 60                  65                  70                  75 ggt act gcc tac aat cag aag ttc aag ggc aag gcc acg ctg acc gcg    292
Gly Thr Ala Tyr Asn Gln Lys Phe Lys Gly Lys Ala Thr Leu Thr Ala
                80                  85                  90 gac aaa tcc act agt aca gcc tac atg gag ctg agc agc ctg aca tct    340
Asp Lys Ser Thr Ser Thr Ala Tyr Met Glu Leu Ser Ser Leu Thr Ser
            95                 100                 105 gag gac acg gcc gtg tat tac tgt aca aga att act ggg tac ttc gat    388
Glu Asp Thr Ala Val Tyr Tyr Cys Thr Arg Ile Thr Gly Tyr Phe Asp
        110                 115                 120 gtc tgg ggg caa ggg acc acg gtc acc gtc tcc tca ggtgagtgga         434
Val Trp Gly Gln Gly Thr Thr Val Thr Val Ser Ser
    125                 130                 135 tccgcga                                                            441
```

<210> SEQ ID NO 18
<211> LENGTH: 135
<212> TYPE: PRT
<213> ORGANISM: Artificial

<220> FEATURE:
<223> OTHER INFORMATION: Synthetic Construct

<400> SEQUENCE: 18

Met Glu Trp Ser Trp Ile Phe Leu Phe Leu Leu Ser Val Thr Ala Gly
1               5                   10                  15

Val Gln Ser Gln Val Gln Leu Val Gln Ser Gly Ala Glu Leu Val Arg
            20                  25                  30

Pro Gly Ser Ser Val Lys Val Ser Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile His Pro Gly Arg Gly Gly Thr Ala Tyr Asn
65                  70                  75                  80

Gln Lys Phe Lys Gly Lys Ala Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Ile Thr Gly Tyr Phe Asp Val Trp Gly Gln Gly
        115                 120                 125

Thr Thr Val Thr Val Ser Ser
    130                 135

<210> SEQ ID NO 19
<211> LENGTH: 455
<212> TYPE: DNA
<213> ORGANISM: Artificial
<220> FEATURE:
<223> OTHER INFORMATION: R2K1-VL1.7 depicted in Fig.3
<220> FEATURE:
<221> NAME/KEY: CDS
<222> LOCATION: (20)..(415)

<400> SEQUENCE: 19
cagcaagctt gccgccacc atg aag ttg cct gtt agg ctg ttg gtg ctg atg        52
                    Met Lys Leu Pro Val Arg Leu Leu Val Leu Met
                    1               5                   10 ttc tgg att cct gct tcc agc agt gat gtt gtg atg act cag tct cca       100
Phe Trp Ile Pro Ala Ser Ser Ser Asp Val Val Met Thr Gln Ser Pro
            15                  20                  25 ctc tcc ctg agc gtc acc ctt gga cag ccg gcc tcc atc tcc tgc agg       148
Leu Ser Leu Ser Val Thr Leu Gly Gln Pro Ala Ser Ile Ser Cys Arg
        30                  35                  40 agc tct caa agc att gta cat agt aat gga aac acc tat ttg gaa tgg       196
Ser Ser Gln Ser Ile Val His Ser Asn Gly Asn Thr Tyr Leu Glu Trp
    45                  50                  55 tac ctg cag aag cca ggg cag tct cca cag ctc ctg atc tat aaa gtt       244
Tyr Leu Gln Lys Pro Gly Gln Ser Pro Gln Leu Leu Ile Tyr Lys Val
60                  65                  70                  75 tcc aac cga ttt tct ggg gtc cca gac aga ttc agc ggc agt ggg tca       292
Ser Asn Arg Phe Ser Gly Val Pro Asp Arg Phe Ser Gly Ser Gly Ser
                80                  85                  90 ggc act gat ttc aca ctg aaa atc agc agg gtt gaa gct gaa gac gtc       340
Gly Thr Asp Phe Thr Leu Lys Ile Ser Arg Val Glu Ala Glu Asp Val
            95                  100                 105 gga gtt tat tac tgc ttt caa ggt tca cat gtt ccg ctc acg ttt ggc       388
Gly Val Tyr Tyr Cys Phe Gln Gly Ser His Val Pro Leu Thr Phe Gly
        110                 115                 120 cag ggg acc aag ctg gag atc aaa cgt gagtagaatt taaactttgc             435
Gln Gly Thr Lys Leu Glu Ile Lys Arg
    125                 130

```
                125                 130
ttcctcagtt ggatccgcga                                                     455

<210> SEQ ID NO 20
<211> LENGTH: 132
<212> TYPE: PRT
<213> ORGANISM: Artificial
<220> FEATURE:
<223> OTHER INFORMATION: Synthetic Construct

<400> SEQUENCE: 20

Met Lys Leu Pro Val Arg Leu Leu Val Leu Met Phe Trp Ile Pro Ala
1               5                   10                  15

Ser Ser Ser Asp Val Val Met Thr Gln Ser Pro Leu Ser Leu Ser Val
            20                  25                  30

Thr Leu Gly Gln Pro Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Phe Gln Gly Ser His Val Pro Leu Thr Phe Gly Gln Gly Thr Lys Leu
        115                 120                 125

Glu Ile Lys Arg
    130

<210> SEQ ID NO 21
<211> LENGTH: 455
<212> TYPE: DNA
<213> ORGANISM: Artificial
<220> FEATURE:
<223> OTHER INFORMATION: R2K1-VL1.8 depicted in Fig.4
<220> FEATURE:
<221> NAME/KEY: CDS
<222> LOCATION: (20)..(415)

<400> SEQUENCE: 21
cagcaagctt gccgccacc atg aag ttg cct gtt agg ctg ttg gtg ctg atg       52
                    Met Lys Leu Pro Val Arg Leu Leu Val Leu Met
                    1               5                   10 ttc tgg att cct gct tcc agc agt gat gtt gtg atg act cag tct cca      100
Phe Trp Ile Pro Ala Ser Ser Ser Asp Val Val Met Thr Gln Ser Pro
            15                  20                  25 ctc tcc ctg ccc gtc acc ctt gga cag ccg gcc tcc atc tcc tgc agg      148
Leu Ser Leu Pro Val Thr Leu Gly Gln Pro Ala Ser Ile Ser Cys Arg
        30                  35                  40 agc tct caa agc att gta cat agt aat gga aac acc tat ttg gaa tgg      196
Ser Ser Gln Ser Ile Val His Ser Asn Gly Asn Thr Tyr Leu Glu Trp
    45                  50                  55 tac ctg cag aag cca ggg cag tct cca cag ctc ctg atc tat aaa gtt      244
Tyr Leu Gln Lys Pro Gly Gln Ser Pro Gln Leu Leu Ile Tyr Lys Val
60                  65                  70                  75 tcc aac cga ttt tct ggg gtc cca gac aga ttc agc ggc agt ggg tca      292
Ser Asn Arg Phe Ser Gly Val Pro Asp Arg Phe Ser Gly Ser Gly Ser
                80                  85                  90 ggc act gat ttc aca ctg aaa atc agc agg gtt gaa gct gaa gac gtc      340
```

```
Gly Thr Asp Phe Thr Leu Lys Ile Ser Arg Val Glu Ala Glu Asp Val
            95                  100                 105 gga gtt tat tac tgc ttt caa ggt tca cat gtt ccg ctc acg ttt ggc     388
Gly Val Tyr Tyr Cys Phe Gln Gly Ser His Val Pro Leu Thr Phe Gly
        110                 115                 120 cag ggg acc aag ctg gag atc aaa cgt gagtagaatt taaactttgc           435
Gln Gly Thr Lys Leu Glu Ile Lys Arg
    125                 130 ttcctcagtt ggatccgcga                                               455

<210> SEQ ID NO 22
<211> LENGTH: 132
<212> TYPE: PRT
<213> ORGANISM: Artificial
<220> FEATURE:
<223> OTHER INFORMATION: Synthetic Construct

<400> SEQUENCE: 22

Met Lys Leu Pro Val Arg Leu Leu Val Leu Met Phe Trp Ile Pro Ala
1               5                   10                  15

Ser Ser Ser Asp Val Val Met Thr Gln Ser Pro Leu Ser Leu Pro Val
            20                  25                  30

Thr Leu Gly Gln Pro Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Phe Gln Gly Ser His Val Pro Leu Thr Phe Gly Gln Gly Thr Lys Leu
        115                 120                 125

Glu Ile Lys Arg
    130

<210> SEQ ID NO 23
<211> LENGTH: 314
<212> TYPE: PRT
<213> ORGANISM: Homo sapiens

<400> SEQUENCE: 23

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110
```

```
Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310

<210> SEQ ID NO 24
<211> LENGTH: 1338
<212> TYPE: DNA
<213> ORGANISM: Artificial
<220> FEATURE:
<223> OTHER INFORMATION: R2K1v1.7 H chain
<220> FEATURE:
<221> NAME/KEY: CDS
<222> LOCATION: (1)..(1338)

<400> SEQUENCE: 24 cag gtg cag ctg cag cag tct ggg gct gag gtg aag aag cct ggg gcc      48
Gln Val Gln Leu Gln Gln Ser Gly Ala Glu Val Lys Lys Pro Gly Ala
1               5                   10                  15 tcc gtg aag gtc tcc tgc aag gct ttg ggg tat acc ttc act gac tat      96
Ser Val Lys Val Ser Cys Lys Ala Leu Gly Tyr Thr Phe Thr Asp Tyr
            20                  25                  30 gaa atg cac tgg gtg aag cag acc cct gta cat ggg ctt gag tgg att     144
Glu Met His Trp Val Lys Gln Thr Pro Val His Gly Leu Glu Trp Ile
        35                  40                  45 gga gct att cat cca gga aga ggt ggt act gcc tac aat cag aag ttc     192
Gly Ala Ile His Pro Gly Arg Gly Gly Thr Ala Tyr Asn Gln Lys Phe
    50                  55                  60 aag ggc aag gcc acg ctg acc gcg gac aaa tcc act agt aca gcc tac     240
Lys Gly Lys Ala Thr Leu Thr Ala Asp Lys Ser Thr Ser Thr Ala Tyr
65                  70                  75                  80 atg gag ctg agc agc ctg aca tct gag gac acg gcc gtg tat tac tgt     288
Met Glu Leu Ser Ser Leu Thr Ser Glu Asp Thr Ala Val Tyr Tyr Cys
                85                  90                  95 aca aga att act ggg tac ttc gat gtc tgg ggg caa ggg acc acg gtc     336
Thr Arg Ile Thr Gly Tyr Phe Asp Val Trp Gly Gln Gly Thr Thr Val
            100                 105                 110
```

-continued

| | |
|---|---|
| acc gtc tcc tca gcc tcc acc aag ggc cca tcg gtc ttc ccc ctg gca<br>Thr Val Ser Ser Ala Ser Thr Lys Gly Pro Ser Val Phe Pro Leu Ala<br>115                    120                   125 | 384 |
| ccc tcc tcc aag agc acc tct ggg ggc aca gcg gcc ctg ggc tgc ctg<br>Pro Ser Ser Lys Ser Thr Ser Gly Gly Thr Ala Ala Leu Gly Cys Leu<br>130                   135                 140 | 432 |
| gtc aag gac tac ttc ccc gaa ccg gtg acg gtg tcg tgg aac tca ggc<br>Val Lys Asp Tyr Phe Pro Glu Pro Val Thr Val Ser Trp Asn Ser Gly<br>145                     150                 155                 160 | 480 |
| gcc ctg acc agc ggc gtg cac acc ttc ccg gct gtc cta cag tcc tca<br>Ala Leu Thr Ser Gly Val His Thr Phe Pro Ala Val Leu Gln Ser Ser<br>                 165                 170                 175 | 528 |
| gga ctc tac tcc ctc agc agc gtg gtg acc gtg ccc tcc agc agc ttg<br>Gly Leu Tyr Ser Leu Ser Ser Val Val Thr Val Pro Ser Ser Ser Leu<br>        180                    185                 190 | 576 |
| ggc acc cag acc tac atc tgc aac gtg aat cac aag ccc agc aac acc<br>Gly Thr Gln Thr Tyr Ile Cys Asn Val Asn His Lys Pro Ser Asn Thr<br>195                    200                 205 | 624 |
| aag gtg gac aag aaa gtt gag ccc aaa tct tgt gac aaa act cac aca<br>Lys Val Asp Lys Lys Val Glu Pro Lys Ser Cys Asp Lys Thr His Thr<br>210                    215                 220 | 672 |
| tgc cca ccg tgc cca gca cct gaa ctc ctg ggg gga ccg tca gtc ttc<br>Cys Pro Pro Cys Pro Ala Pro Glu Leu Leu Gly Gly Pro Ser Val Phe<br>225                     230                 235                 240 | 720 |
| ctc ttc ccc cca aaa ccc aag gac acc ctc atg atc tcc cgg acc cct<br>Leu Phe Pro Pro Lys Pro Lys Asp Thr Leu Met Ile Ser Arg Thr Pro<br>                 245                 250                 255 | 768 |
| gag gtc aca tgc gtg gtg gtg gac gtg agc cac gaa gac cct gag gtc<br>Glu Val Thr Cys Val Val Val Asp Val Ser His Glu Asp Pro Glu Val<br>        260                    265                 270 | 816 |
| aag ttc aac tgg tac gtg gac ggc gtg gag gtg cat aat gcc aag aca<br>Lys Phe Asn Trp Tyr Val Asp Gly Val Glu Val His Asn Ala Lys Thr<br>275                     280                 285 | 864 |
| aag ccg cgg gag gag cag tac aac agc acg tac cgt gtg gtc agc gtc<br>Lys Pro Arg Glu Glu Gln Tyr Asn Ser Thr Tyr Arg Val Val Ser Val<br>290                     295                 300 | 912 |
| ctc acc gtc ctg cac cag gac tgg ctg aat ggc aag gag tac aag tgc<br>Leu Thr Val Leu His Gln Asp Trp Leu Asn Gly Lys Glu Tyr Lys Cys<br>305                     310                 315                 320 | 960 |
| aag gtc tcc aac aaa gcc ctc cca gcc ccc atc gag aaa acc atc tcc<br>Lys Val Ser Asn Lys Ala Leu Pro Ala Pro Ile Glu Lys Thr Ile Ser<br>                 325                 330                 335 | 1008 |
| aaa gcc aaa ggg cag ccc cga gaa cca cag gtg tac acc ctg ccc cca<br>Lys Ala Lys Gly Gln Pro Arg Glu Pro Gln Val Tyr Thr Leu Pro Pro<br>        340                    345                 350 | 1056 |
| tcc cgg gat gag ctg acc aag aac cag gtc agc ctg acc tgc ctg gtc<br>Ser Arg Asp Glu Leu Thr Lys Asn Gln Val Ser Leu Thr Cys Leu Val<br>355                     360                 365 | 1104 |
| aaa ggc ttc tat ccc agc gac atc gcc gtg gag tgg gag agc aat ggg<br>Lys Gly Phe Tyr Pro Ser Asp Ile Ala Val Glu Trp Glu Ser Asn Gly<br>370                     375                 380 | 1152 |
| cag ccg gag aac aac tac aag acc acg cct ccc gtg ctg gac tcc gac<br>Gln Pro Glu Asn Asn Tyr Lys Thr Thr Pro Pro Val Leu Asp Ser Asp<br>385                     390                 395                 400 | 1200 |
| ggc tcc ttc ttc ctc tac agc aag ctc acc gtg gac aag agc agg tgg<br>Gly Ser Phe Phe Leu Tyr Ser Lys Leu Thr Val Asp Lys Ser Arg Trp<br>                 405                 410                 415 | 1248 |
| cag cag ggg aac gtc ttc tca tgc tcc gtg atg cat gag gct ctg cac<br>Gln Gln Gly Asn Val Phe Ser Cys Ser Val Met His Glu Ala Leu His | 1296 |

-continued

```
                420                 425                 430
aac cac tac acg cag aag agc ctc tcc ctg tct ccg ggt aaa                    1338
Asn His Tyr Thr Gln Lys Ser Leu Ser Leu Ser Pro Gly Lys
        435                 440                 445

<210> SEQ ID NO 25
<211> LENGTH: 446
<212> TYPE: PRT
<213> ORGANISM: Artificial
<220> FEATURE:
<223> OTHER INFORMATION: Synthetic Construct

<400> SEQUENCE: 25
```

Gln Val Gln Leu Gln Gln Ser Gly Ala Glu Val Lys Lys Pro Gly Ala
1               5                   10                  15

Ser Val Lys Val Ser Cys Lys Ala Leu Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile His Pro Gly Arg Gly Gly Thr Ala Tyr Asn Gln Lys Phe
    50                  55                  60

Lys Gly Lys Ala Thr Leu Thr Ala Asp Lys Ser Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Ile Thr Gly Tyr Phe Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

```
Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 26
<211> LENGTH: 657
<212> TYPE: DNA
<213> ORGANISM: Artificial
<220> FEATURE:
<223> OTHER INFORMATION: R2K1v1.7 L chain
<220> FEATURE:
<221> NAME/KEY: CDS
<222> LOCATION: (1)..(657)

<400> SEQUENCE: 26
```

| | | |
|---|---|---|
| gat gtt gtg atg act cag tct cca ctc tcc ctg agc gtc acc ctt gga<br>Asp Val Val Met Thr Gln Ser Pro Leu Ser Leu Ser Val Thr Leu Gly<br>1               5                   10                  15 | 48 |
| cag ccg gcc tcc atc tcc tgc agg agc tct caa agc att gta cat agt<br>Gln Pro Ala Ser Ile Ser Cys Arg Ser Ser Gln Ser Ile Val His Ser<br>            20                  25                  30 | 96 |
| aat gga aac acc tat ttg gaa tgg tac ctg cag aag cca ggg cag tct<br>Asn Gly Asn Thr Tyr Leu Glu Trp Tyr Leu Gln Lys Pro Gly Gln Ser<br>        35                  40                  45 | 144 |
| cca cag ctc ctg atc tat aaa gtt tcc aac cga ttt tct ggg gtc cca<br>Pro Gln Leu Leu Ile Tyr Lys Val Ser Asn Arg Phe Ser Gly Val Pro<br>    50                  55                  60 | 192 |
| gac aga ttc agc ggc agt ggg tca ggc act gat ttc aca ctg aaa atc<br>Asp Arg Phe Ser Gly Ser Gly Ser Gly Thr Asp Phe Thr Leu Lys Ile<br>65                  70                  75                  80 | 240 |
| agc agg gtt gaa gct gaa gac gtc gga gtt tat tac tgc ttt caa ggt<br>Ser Arg Val Glu Ala Glu Asp Val Gly Val Tyr Tyr Cys Phe Gln Gly<br>                85                  90                  95 | 288 |
| tca cat gtt ccg ctc acg ttt ggc cag ggg acc aag ctg gag atc aaa<br>Ser His Val Pro Leu Thr Phe Gly Gln Gly Thr Lys Leu Glu Ile Lys<br>            100                 105                 110 | 336 |
| cga act gtg gct gca cca tct gtc ttc atc ttc ccg cca tct gat gag<br>Arg Thr Val Ala Ala Pro Ser Val Phe Ile Phe Pro Pro Ser Asp Glu<br>        115                 120                 125 | 384 |
| cag ttg aaa tct gga act gcc tct gtt gtg tgc ctg ctg aat aac ttc<br>Gln Leu Lys Ser Gly Thr Ala Ser Val Val Cys Leu Leu Asn Asn Phe<br>    130                 135                 140 | 432 |
| tat ccc aga gag gcc aaa gta cag tgg aag gtg gat aac gcc ctc caa<br>Tyr Pro Arg Glu Ala Lys Val Gln Trp Lys Val Asp Asn Ala Leu Gln<br>145                 150                 155                 160 | 480 |
| tcg ggt aac tcc cag gag agt gtc aca gag cag gac agc aag gac agc<br>Ser Gly Asn Ser Gln Glu Ser Val Thr Glu Gln Asp Ser Lys Asp Ser<br>                165                 170                 175 | 528 |
| acc tac agc ctc agc agc acc ctg acg ctg agc aaa gca gac tac gag<br> | 576 |

-continued

```
Thr Tyr Ser Leu Ser Ser Thr Leu Thr Leu Ser Lys Ala Asp Tyr Glu
            180                 185                 190 aaa cac aaa gtc tac gcc tgc gaa gtc acc cat cag ggc ctg agc tcg      624
Lys His Lys Val Tyr Ala Cys Glu Val Thr His Gln Gly Leu Ser Ser
        195                 200                 205 ccc gtc aca aag agc ttc aac agg gga gag tgt                          657
Pro Val Thr Lys Ser Phe Asn Arg Gly Glu Cys
        210                 215

<210> SEQ ID NO 27
<211> LENGTH: 219
<212> TYPE: PRT
<213> ORGANISM: Artificial
<220> FEATURE:
<223> OTHER INFORMATION: Synthetic Construct

<400> SEQUENCE: 27

Asp Val Val Met Thr Gln Ser Pro Leu Ser Leu Ser Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```